United States Patent
Lin et al.

(10) Patent No.: US 11,674,172 B2
(45) Date of Patent: Jun. 13, 2023

(54) PIRNA-54265 DETECTION KIT USED FOR EARLY SCREENING, DIAGNOSIS, CURATIVE EFFICACY MONITORING AND PROGNOSTIC EVALUATION OF COLORECTAL CANCER

(71) Applicants: SUN YAT-SEN UNIVERSITY, Guangdong (CN); SUN YAT-SEN UNIVERSITY CANCER CENTER, Guangdong (CN)

(72) Inventors: Dongxin Lin, Guangdong (CN); Jian Zheng, Guangdong (CN); Dongmei Mai, Guangdong (CN); Liping Tan, Guangdong (CN)

(73) Assignees: SUN YAT-SEN UNIVERSITY, Guangdong (CN); SUN YAT-SEN UNIVERSITY CANCER CENTER, Guangdong (CN)

( * ) Notice: Subject to any disclaimer, the term of this patent is extended or adjusted under 35 U.S.C. 154(b) by 0 days.

(21) Appl. No.: 17/830,354

(22) Filed: Jun. 2, 2022

(65) Prior Publication Data
US 2022/0298556 A1    Sep. 22, 2022

Related U.S. Application Data

(60) Division of application No. 16/576,746, filed on Sep. 19, 2019, now abandoned, which is a continuation-in-part of application No. PCT/CN2018/096398, filed on Jul. 20, 2018.

(30) Foreign Application Priority Data

Feb. 12, 2018 (CN) .......................... 201810146715.6
Jan. 15, 2019 (CN) ......................... 201910036674.X

(51) Int. Cl.
*C12Q 1/6827* (2018.01)

(52) U.S. Cl.
CPC ..... *C12Q 1/6827* (2013.01); *C12Q 2600/166* (2013.01); *C12Q 2600/178* (2013.01)

(58) Field of Classification Search
None
See application file for complete search history.

(56) References Cited

FOREIGN PATENT DOCUMENTS

CN        108103202       6/2018

OTHER PUBLICATIONS

Dongmei Mai et al., "PIWI-interacting RNA-54265 is oncogenic and a potential therapeutic target in colorectal adenocarcinoma", Theranostics, vol. 8, Oct. 2018, pp. 1-54.
Runshi Gao et al., "Strategies for primer design in detection of MicroRNA by stem-loop and polyA-tailed PGR", Journal of Toxicology, vol. 26, Oct. 2012, with English abstract thereof, pp. 1-5.

*Primary Examiner* — Amanda Haney
(74) *Attorney, Agent, or Firm* — JCIPRNET

(57) ABSTRACT

The present invention relates to a piRNA-54265 detection kit used for early screening, diagnosis, efficacy monitoring and/or prognostic evaluation of colorectal cancer. The detection kit includes a primers combination, including a primer pair and a probe for specifically detecting piRNA-54265; the primer pair is a piRNA-54265 stem-loop PCR primer pair, or a piRNA-54265 PolyA tailed PCR primer pair; the primer pair includes a forward primer and a reverse primer.

8 Claims, 18 Drawing Sheets

Specification includes a Sequence Listing.

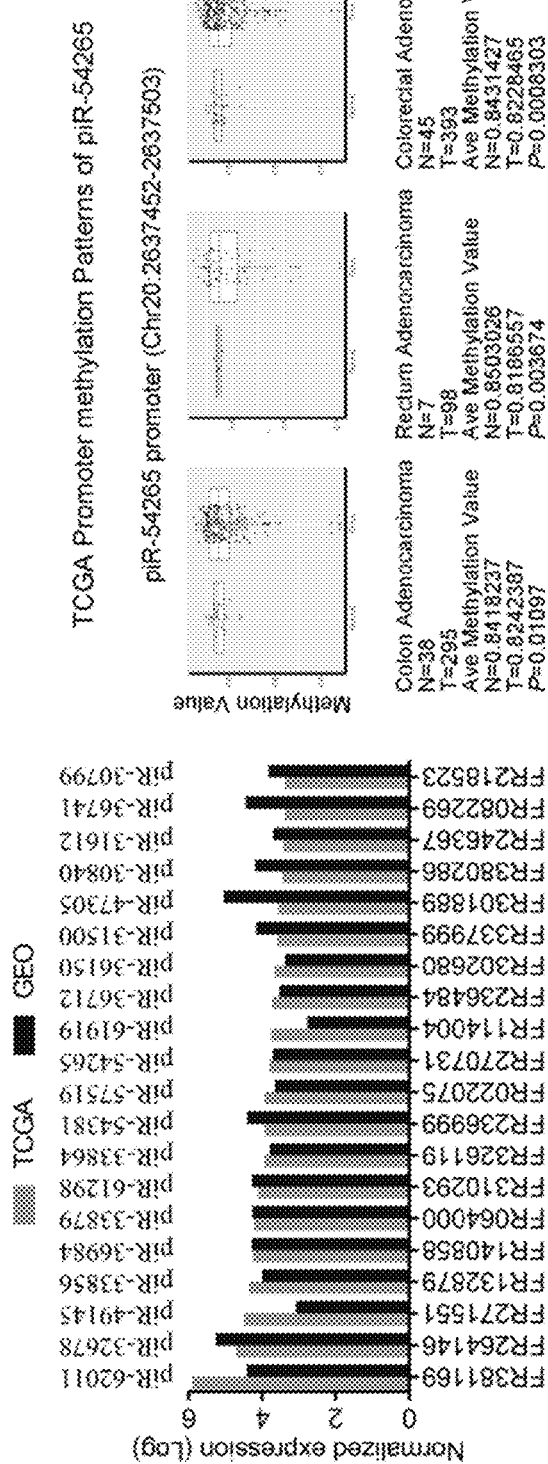
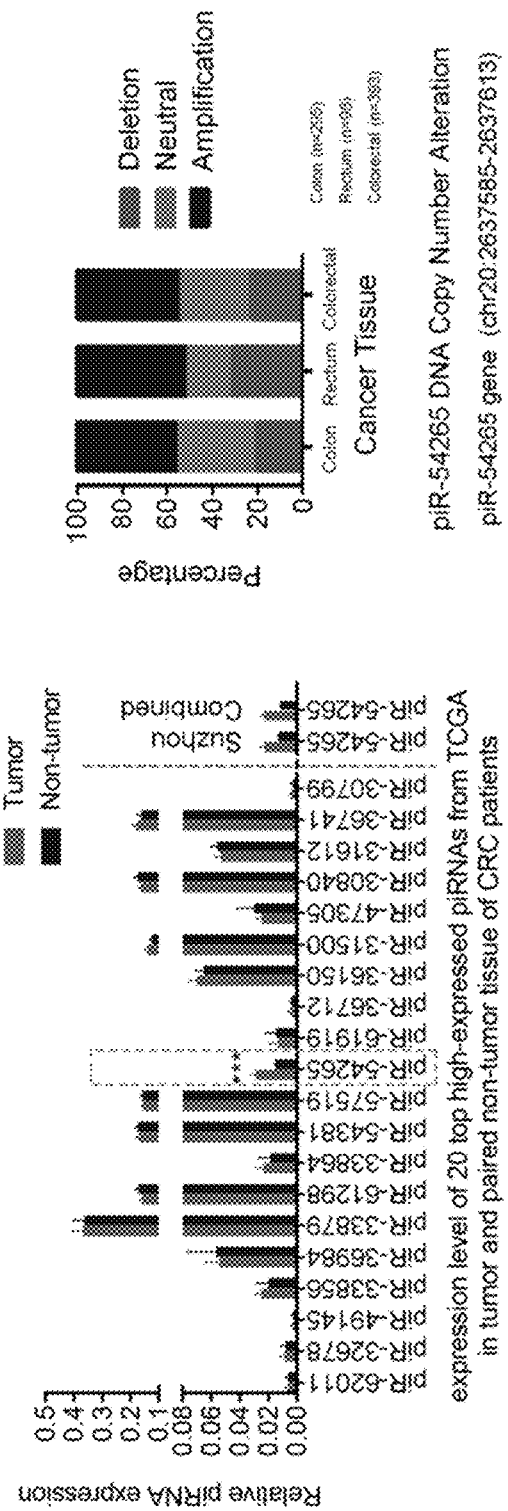
FIG. 1a
FIG. 1b
FIG. 1c
FIG. 1d

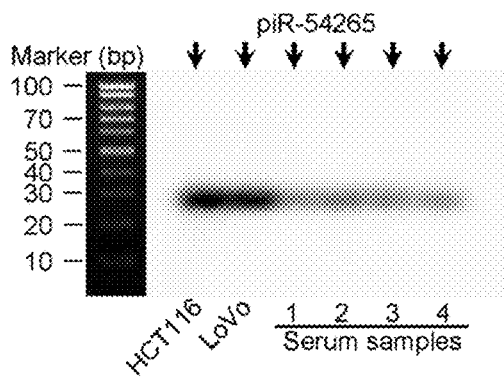
FIG. 3a
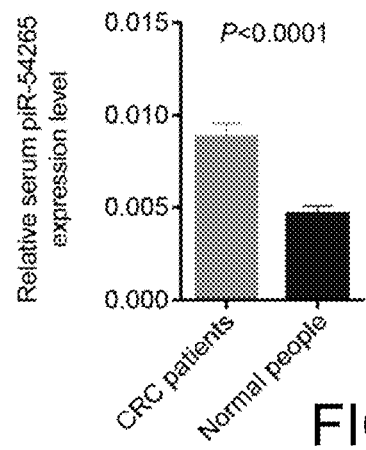
FIG. 3b
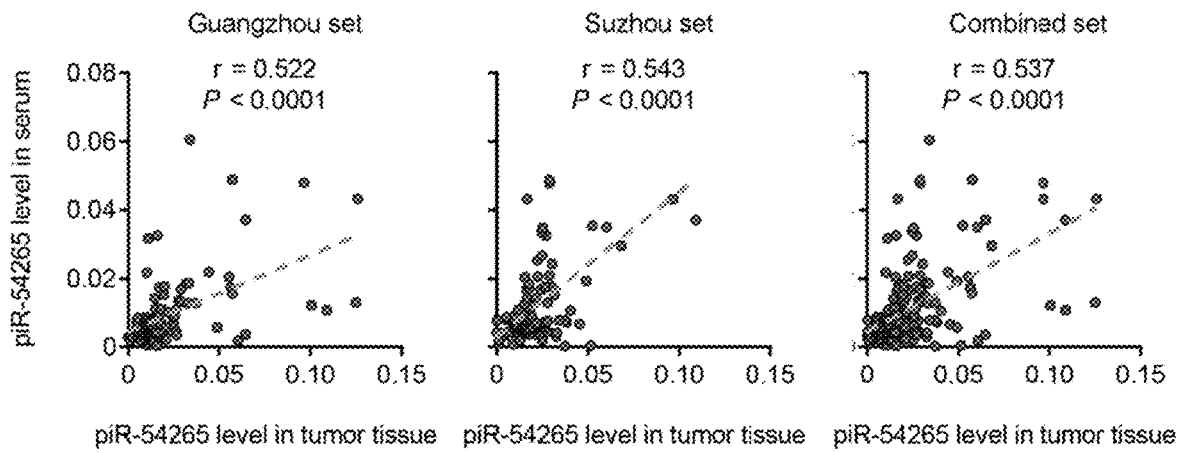
FIG. 3c
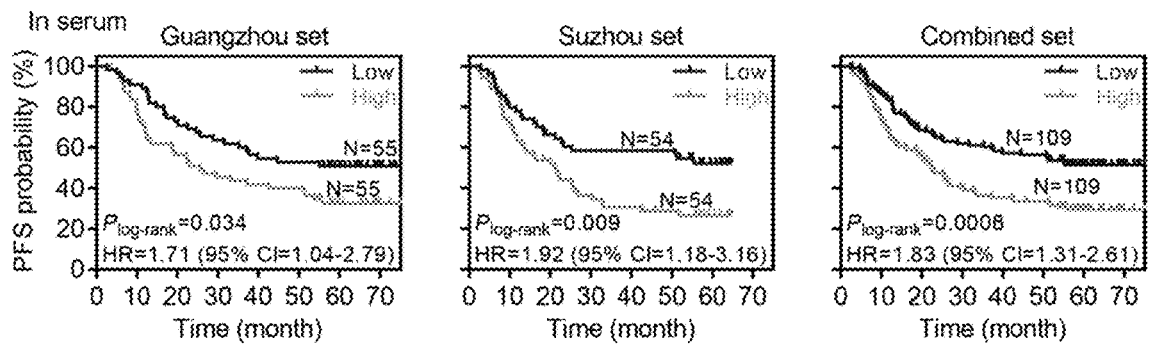
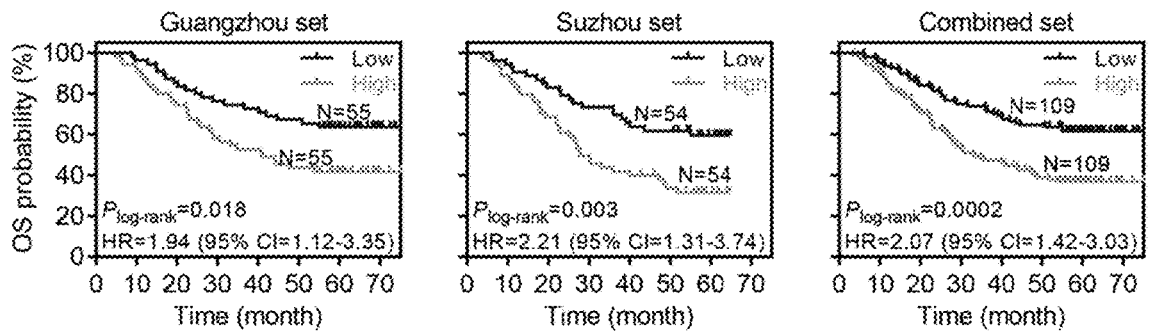
FIG. 3d

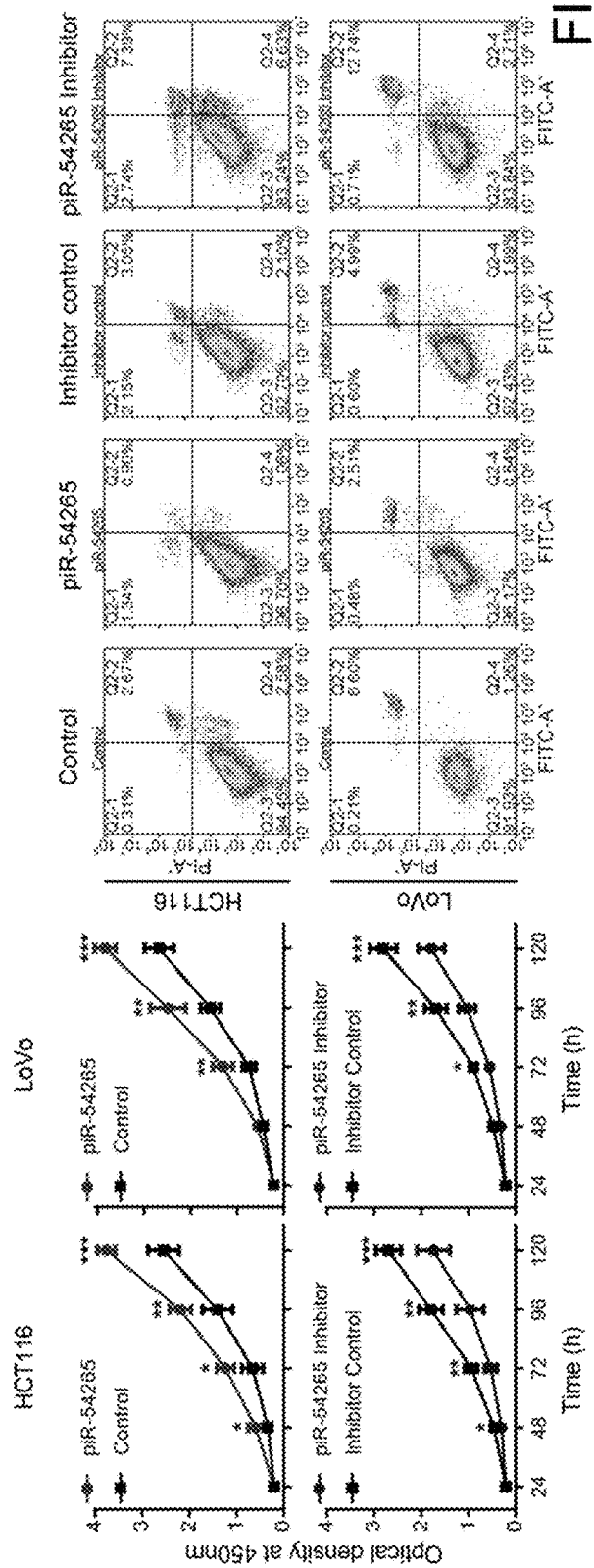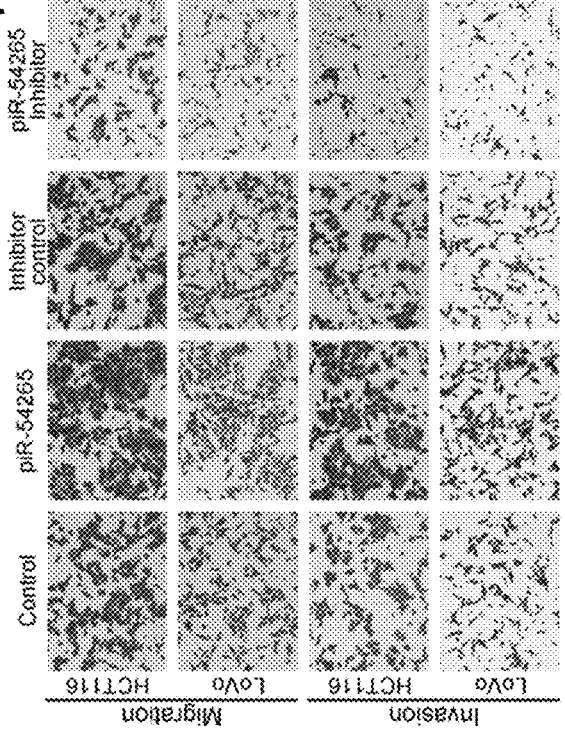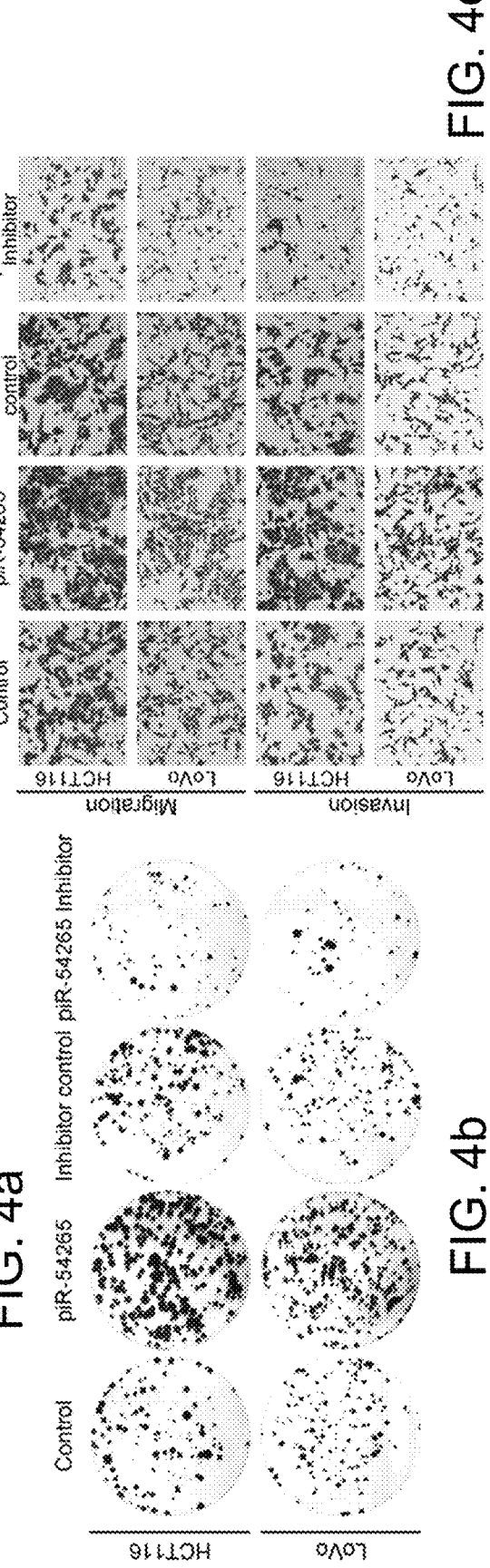
FIG. 4a
FIG. 4b
FIG. 4c
FIG. 4d

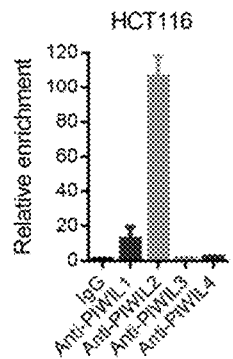
FIG. 6a
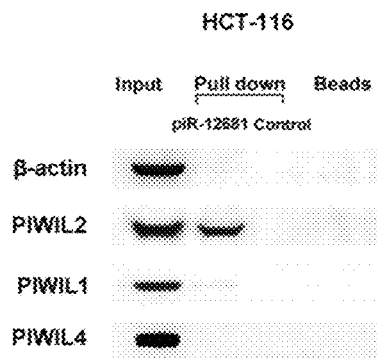
FIG. 6b
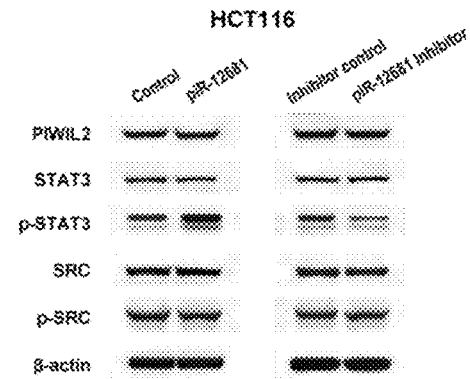
FIG. 6c
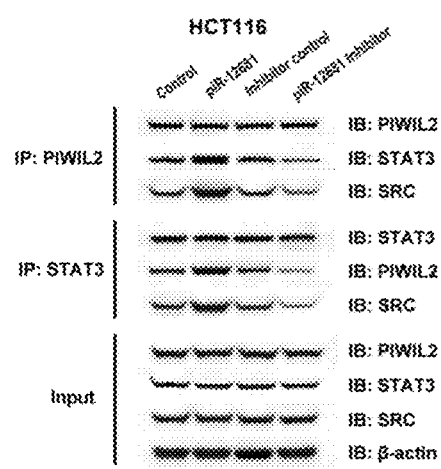
FIG. 6d
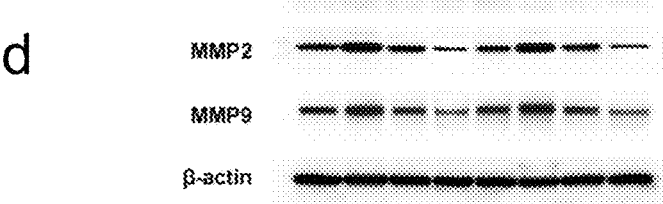
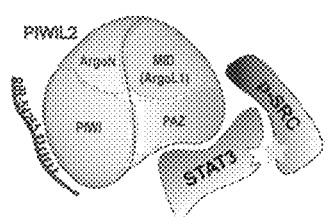
FIG. 6e
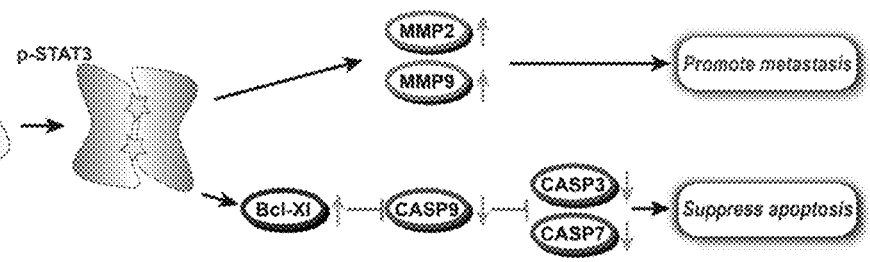
FIG. 6f

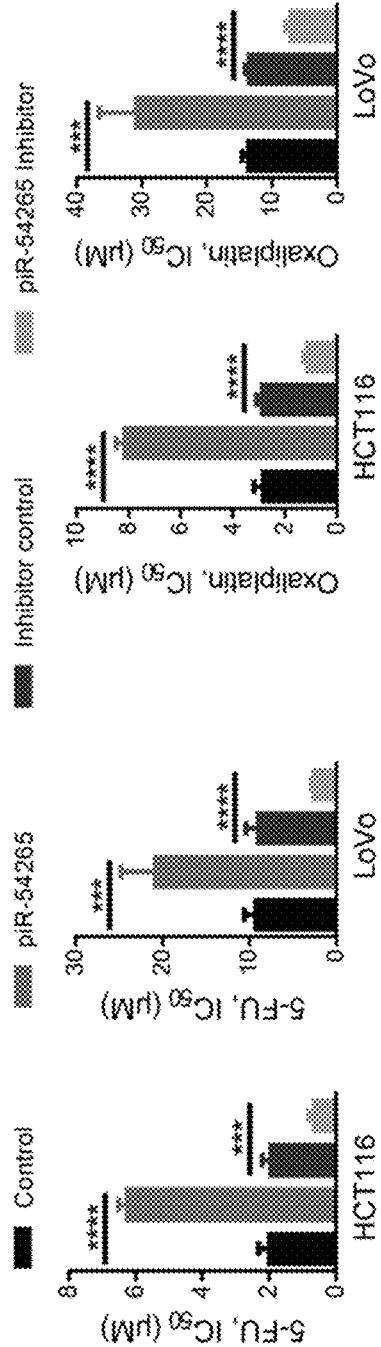
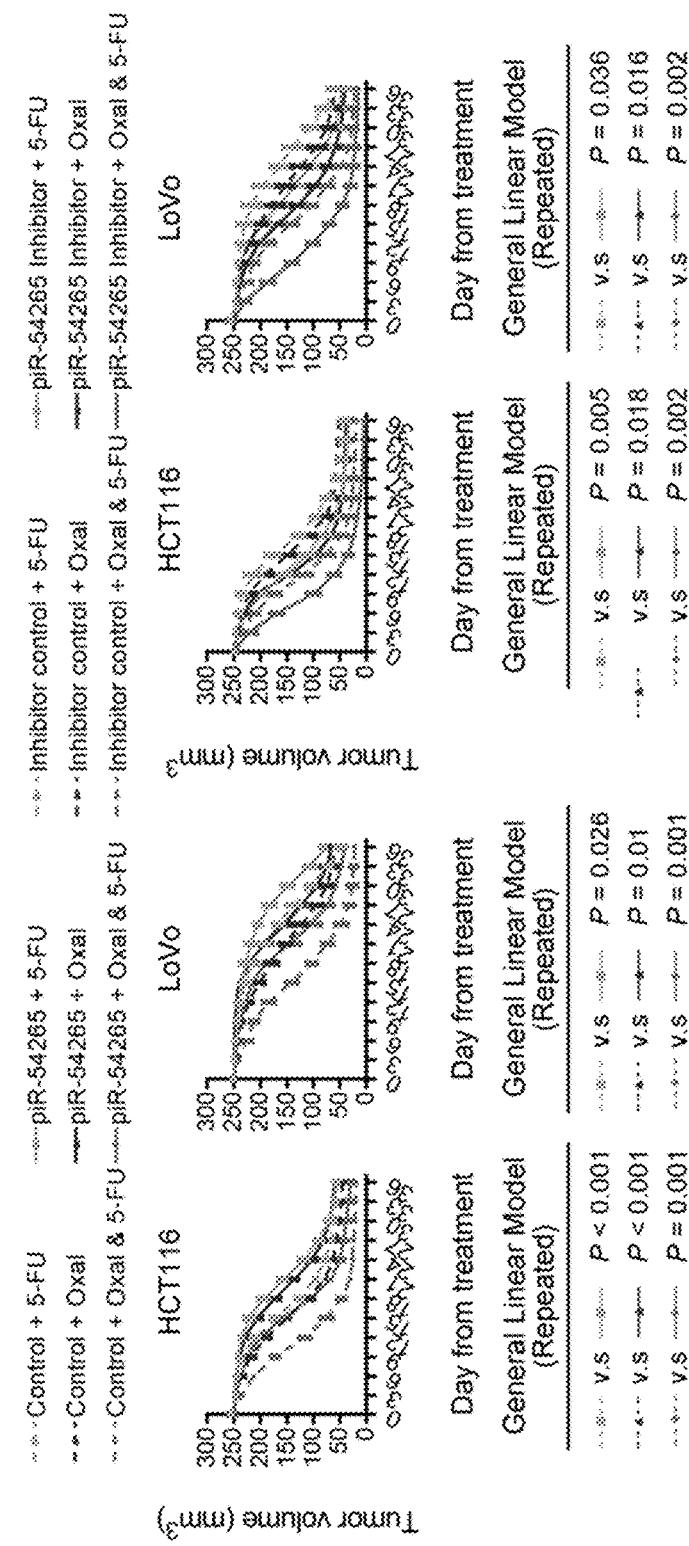
FIG. 7a
FIG. 7b

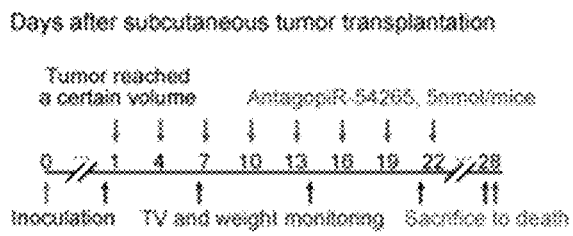
FIG. 8a
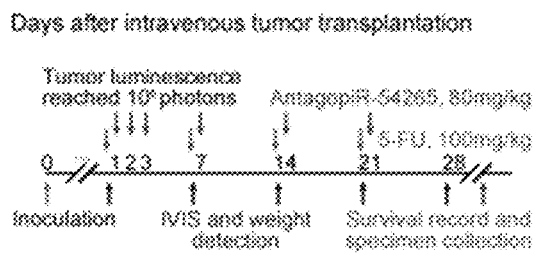
FIG. 8b
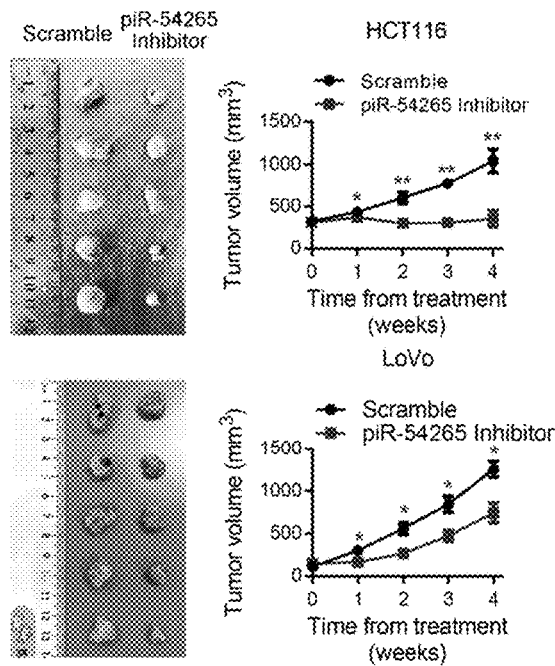
FIG. 8c
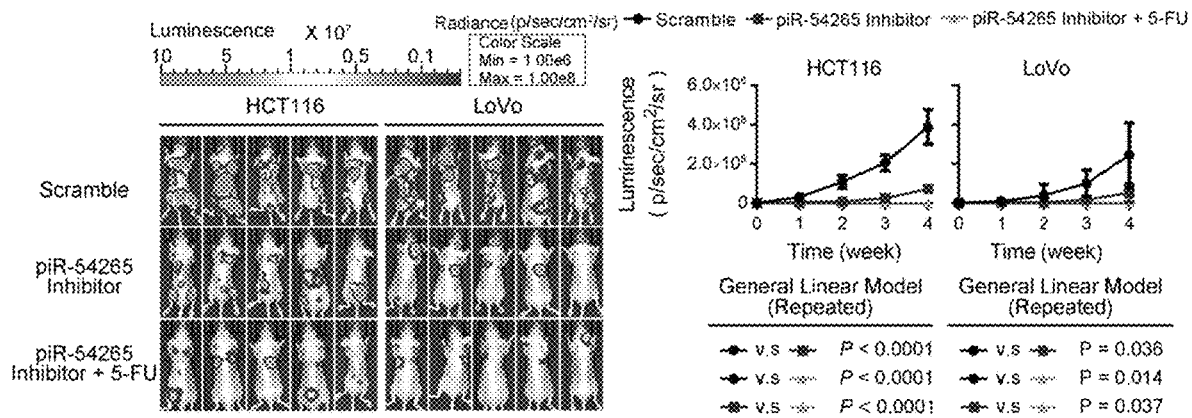
FIG. 8d
FIG. 8e
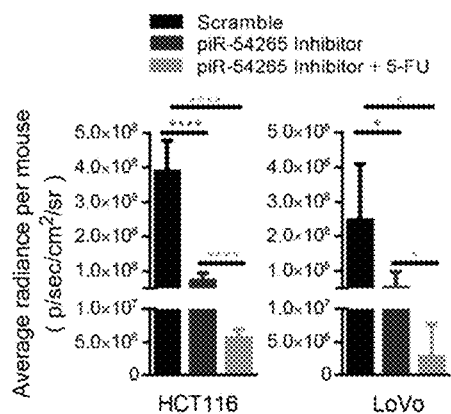
FIG. 8f
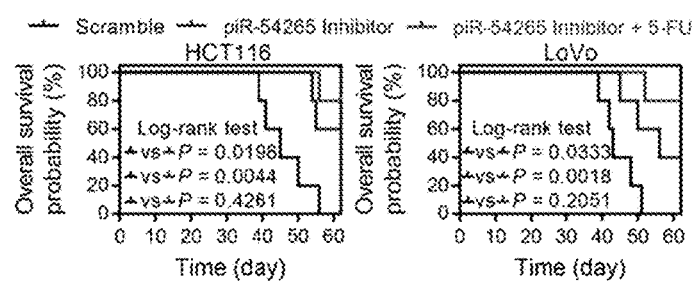
FIG. 8g

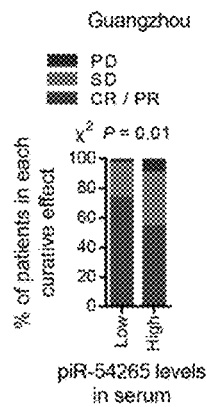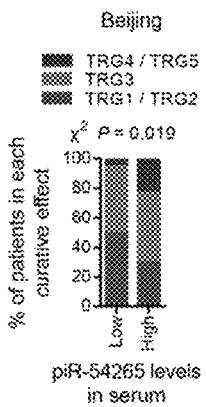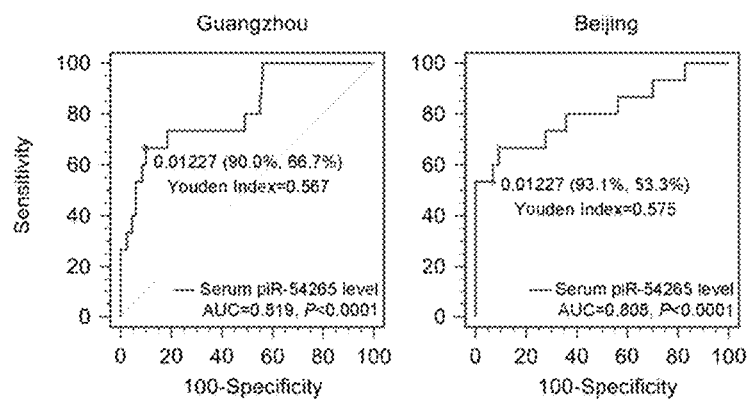
FIG. 9a   FIG. 9b                     FIG. 9c
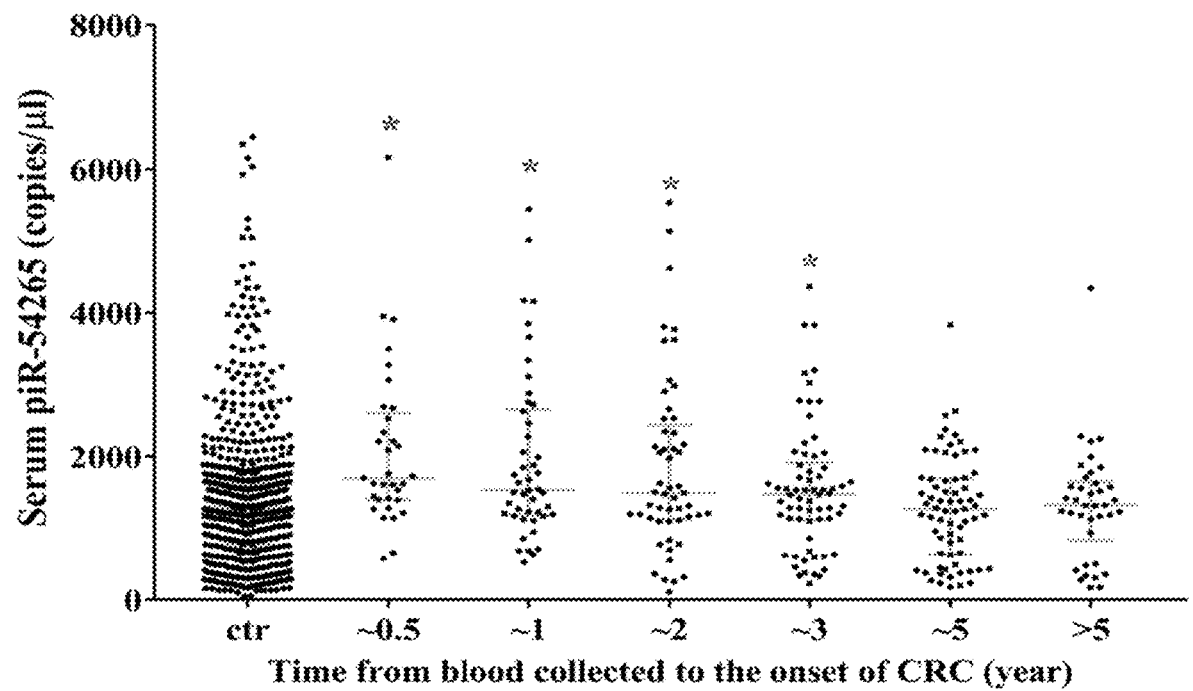
FIG. 10

FIG. 11

SEQUENCE LISTING

```
<160> NUMBER OF SEQ ID NOS: 37

<210> SEQ ID NO 1
<211> LENGTH: 29
<212> TYPE: DNA
<213> ORGANISM: Artificial Sequence
<220> FEATURE:
<223> OTHER INFORMATION: Primer Sequence

<400> SEQUENCE: 1
tggaggtgat gaactgtctg agcctgacc                                    29

<210> SEQ ID NO 2
<211> LENGTH: 67
<212> TYPE: DNA
<213> ORGANISM: Artificial Sequence
<220> FEATURE:
<223> OTHER INFORMATION: Primer Sequence

<400> SEQUENCE: 2
tgaccgtctg tatggttgtt cacgactcct tcaccctatc caaccataca gacggtcagg   60
tcaggct                                                            67

<210> SEQ ID NO 3
<211> LENGTH: 61
<212> TYPE: DNA
<213> ORGANISM: Artificial Sequence
<220> FEATURE:
<223> OTHER INFORMATION: Primer Sequence

<400> SEQUENCE: 3
gctgtcaacg atacgctacg taacggcatg acagtgtttt tttttttttt tttttttttt   60
a                                                                  61

<210> SEQ ID NO 4
<211> LENGTH: 61
<212> TYPE: DNA
<213> ORGANISM: Artificial Sequence
<220> FEATURE:
<223> OTHER INFORMATION: Primer Sequence

<400> SEQUENCE: 4
gctgtcaacg atacgctacg taacggcatg acagtgtttt tttttttttt tttttttttt   60
g                                                                  61
```

-continued

```
<210> SEQ ID NO 5
<211> LENGTH: 61
<212> TYPE: DNA
<213> ORGANISM: Artificial Sequence
<220> FEATURE:
<223> OTHER INFORMATION: Primer Sequence

<400> SEQUENCE: 5
gctgtcaacg atacgctacg taacggcatg acagtgtttt tttttttttt tttttttttt      60
c                                                                      61

<210> SEQ ID NO 6
<211> LENGTH: 22
<212> TYPE: DNA
<213> ORGANISM: Artificial Sequence
<220> FEATURE:
<223> OTHER INFORMATION: Primer Sequence

<400> SEQUENCE: 6
tcaccgggtg taaatcagct tg                                               22

<210> SEQ ID NO 7
<211> LENGTH: 76
<212> TYPE: DNA
<213> ORGANISM: Artificial Sequence
<220> FEATURE:
<223> OTHER INFORMATION: Primer Sequence

<400> SEQUENCE: 7
tgaacatcct ctggaggcca actgcgtgag cttgttactc attttctcag cctccagagg      60
atgttcacaa gctgat                                                      76

<210> SEQ ID NO 8
<211> LENGTH: 29
<212> TYPE: DNA
<213> ORGANISM: Artificial Sequence
<220> FEATURE:
<223> OTHER INFORMATION: Primer Sequence

<400> SEQUENCE: 8
tggaggtgat gaactgtctg agcctgacc                                        29

<210> SEQ ID NO 9
<211> LENGTH: 24
<212> TYPE: DNA
<213> ORGANISM: Artificial Sequence
<220> FEATURE:
<223> OTHER INFORMATION: Primer Sequence

<400> SEQUENCE: 9
tatggttgtt cacgactcct tcac                                             24

<210> SEQ ID NO 10
<211> LENGTH: 25
<212> TYPE: DNA
<213> ORGANISM: Artificial Sequence
<220> FEATURE:
<223> OTHER INFORMATION: Primer Sequence

<400> SEQUENCE: 10
tggaggtgat gaactgtctg agcct                                            25

<210> SEQ ID NO 11
<211> LENGTH: 21
<212> TYPE: DNA
```

<213> ORGANISM: Artificial Sequence
<220> FEATURE:
<223> OTHER INFORMATION: Primer Sequence

<400> SEQUENCE: 11
tggaggtgat gaactgtctg a                                              21

<210> SEQ ID NO 12
<211> LENGTH: 17
<212> TYPE: DNA
<213> ORGANISM: Artificial Sequence
<220> FEATURE:
<223> OTHER INFORMATION: Primer Sequence

<400> SEQUENCE: 12
tggaggtgat gaactgt                                                   17

<210> SEQ ID NO 13
<211> LENGTH: 17
<212> TYPE: DNA
<213> ORGANISM: Artificial Sequence
<220> FEATURE:
<223> OTHER INFORMATION: Primer Sequence

<400> SEQUENCE: 13
tatggttgtt cacgact                                                   17

<210> SEQ ID NO 14
<211> LENGTH: 13
<212> TYPE: DNA
<213> ORGANISM: Artificial Sequence
<220> FEATURE:
<223> OTHER INFORMATION: Primer Sequence

<400> SEQUENCE: 14
tggaggtgat gaa                                                       13

<210> SEQ ID NO 15
<211> LENGTH: 20
<212> TYPE: DNA
<213> ORGANISM: Artificial Sequence
<220> FEATURE:
<223> OTHER INFORMATION: Primer Sequence

<400> SEQUENCE: 15
ctatcgcatg ctggaggtga                                                20

<210> SEQ ID NO 16
<211> LENGTH: 20
<212> TYPE: DNA
<213> ORGANISM: Artificial Sequence
<220> FEATURE:
<223> OTHER INFORMATION: Primer Sequence

<400> SEQUENCE: 16
tcgactatcg catgctggag                                                20

<210> SEQ ID NO 17
<211> LENGTH: 19
<212> TYPE: DNA
<213> ORGANISM: Artificial Sequence
<220> FEATURE:
<223> OTHER INFORMATION: Primer Sequence

<400> SEQUENCE: 17
tcgactatcg catgctgga                                                 19

```
<210> SEQ ID NO 18
<211> LENGTH: 18
<212> TYPE: DNA
<213> ORGANISM: Artificial Sequence
<220> FEATURE:
<223> OTHER INFORMATION: Primer Sequence

<400> SEQUENCE: 18
tcgactatcg catgctgg                                                   18

<210> SEQ ID NO 19
<211> LENGTH: 17
<212> TYPE: DNA
<213> ORGANISM: Artificial Sequence
<220> FEATURE:
<223> OTHER INFORMATION: Primer Sequence

<400> SEQUENCE: 19
tcgactatcg catgctg                                                    17

<210> SEQ ID NO 20
<211> LENGTH: 16
<212> TYPE: DNA
<213> ORGANISM: Artificial Sequence
<220> FEATURE:
<223> OTHER INFORMATION: Primer Sequence

<400> SEQUENCE: 20
tcgactatcg catgct                                                     16

<210> SEQ ID NO 21
<211> LENGTH: 25
<212> TYPE: DNA
<213> ORGANISM: Artificial Sequence
<220> FEATURE:
<223> OTHER INFORMATION: Primer Sequence

<400> SEQUENCE: 21
gctgtcaacg atacgctacg taacg                                           25

<210> SEQ ID NO 22
<211> LENGTH: 20
<212> TYPE: DNA
<213> ORGANISM: Artificial Sequence
<220> FEATURE:
<223> OTHER INFORMATION: Primer Sequence

<400> SEQUENCE: 22
gctgtcaacg atacgctacg                                                 20

<210> SEQ ID NO 23
<211> LENGTH: 15
<212> TYPE: DNA
<213> ORGANISM: Artificial Sequence
<220> FEATURE:
<223> OTHER INFORMATION: Primer Sequence

<400> SEQUENCE: 23
gctgtcaacg atacg                                                      15

<210> SEQ ID NO 24
<211> LENGTH: 20
<212> TYPE: DNA
<213> ORGANISM: Artificial Sequence
<220> FEATURE:
```

```
<223> OTHER INFORMATION: Primer Sequence

<400> SEQUENCE: 24
cggctcaccg ggtgtaaatc                                               20

<210> SEQ ID NO 25
<211> LENGTH: 22
<212> TYPE: DNA
<213> ORGANISM: Artificial Sequence
<220> FEATURE:
<223> OTHER INFORMATION: Primer Sequence

<400> SEQUENCE: 25
caactgcgtg agcttgttac tc                                            22

<210> SEQ ID NO 26
<211> LENGTH: 22
<212> TYPE: DNA
<213> ORGANISM: Artificial Sequence
<220> FEATURE:
<223> OTHER INFORMATION: Primer Sequence

<400> SEQUENCE: 26
cctggaggtg atgaactgtc tg                                            22

<210> SEQ ID NO 27
<211> LENGTH: 27
<212> TYPE: DNA
<213> ORGANISM: Artificial Sequence
<220> FEATURE:
<223> OTHER INFORMATION: Primer Sequence

<400> SEQUENCE: 27
ccctatccaa ccatacagac ggtcagg                                       27

<210> SEQ ID NO 28
<211> LENGTH: 27
<212> TYPE: DNA
<213> ORGANISM: Artificial Sequence
<220> FEATURE:
<223> OTHER INFORMATION: Primer Sequence

<400> SEQUENCE: 28
attttctcag cctccagagg atgttca                                       27

<210> SEQ ID NO 29
<211> LENGTH: 29
<212> TYPE: DNA
<213> ORGANISM: Artificial Sequence
<220> FEATURE:
<223> OTHER INFORMATION: piRNA-54265 Sequence

<400> SEQUENCE: 29
tggaggtgat gaactgtctg agcctgacc                                     29

<210> SEQ ID NO 30
<211> LENGTH: 29
<212> TYPE: RNA
<213> ORGANISM: Artificial Sequence
<220> FEATURE:
<223> OTHER INFORMATION: piRNA-54265 Sequence

<400> SEQUENCE: 30
uggaggugau gaacugucug agccugacc                                     29
```

-continued

```
<210> SEQ ID NO 31
<211> LENGTH: 29
<212> TYPE: RNA
<213> ORGANISM: Artificial Sequence
<220> FEATURE:
<223> OTHER INFORMATION: piRNA-54265 reverse complementary sequence

<400> SEQUENCE: 31
ggucaggcuc agacaguuca ucaccucca                                29

<210> SEQ ID NO 32
<211> LENGTH: 87
<212> TYPE: DNA
<213> ORGANISM: Artificial Sequence
<220> FEATURE:
<223> OTHER INFORMATION: Primer Sequence

<400> SEQUENCE: 32
tgaccgtctg tatggttgtt cacgactcct tcaccctatc caaccataca gacggtcagg   60
tcaggctcag acagttcatc acctcca                                      87

<210> SEQ ID NO 33
<211> LENGTH: 51
<212> TYPE: DNA
<213> ORGANISM: Artificial Sequence
<220> FEATURE:
<223> OTHER INFORMATION: Primer Sequence

<400> SEQUENCE: 33
tggaggtgat gaactgtctg tgaaggagtc gtgaacaacc atactgccag t            51

<210> SEQ ID NO 34
<211> LENGTH: 53
<212> TYPE: DNA
<213> ORGANISM: Artificial Sequence
<220> FEATURE:
<223> OTHER INFORMATION: Primer Sequence

<400> SEQUENCE: 34
tggaggtgat gaactgtctg agcctgacca aaaaaaaaaa aaaaaaaaaa aaa          53

<210> SEQ ID NO 35
<211> LENGTH: 37
<212> TYPE: DNA
<213> ORGANISM: Artificial Sequence
<220> FEATURE:
<223> OTHER INFORMATION: Primer Sequence

<400> SEQUENCE: 35
gctgtgacag tgttttttttt tttttttttt tttttttg                         37

<210> SEQ ID NO 36
<211> LENGTH: 65
<212> TYPE: DNA
<213> ORGANISM: Artificial Sequence
<220> FEATURE:
<223> OTHER INFORMATION: Artificial Sequence

<400> SEQUENCE: 36
gctgtgacag tgttttttttt tttttttttt tttttggtc aggctcagac agttcatcac   60
ctcca                                                              65

<210> SEQ ID NO 37
<211> LENGTH: 44
<212> TYPE: DNA
```

```
<213> ORGANISM: Artificial Sequence
<220> FEATURE:
<223> OTHER INFORMATION: Primer Sequence

<400> SEQUENCE: 37
tggaggtgat gaactgtctc gttacgtagc gtatcgttga cagc                    44
```

PIRNA-54265 DETECTION KIT USED FOR EARLY SCREENING, DIAGNOSIS, CURATIVE EFFICACY MONITORING AND PROGNOSTIC EVALUATION OF COLORECTAL CANCER

CROSS-REFERENCE TO RELATED APPLICATION

This application is a divisional of an application Ser. No. 16/576,746, filed on Sep. 19, 2019, now pending. The prior application Ser. No. 16/576,746 is a continuation-in-part application of International Application No. PCT/CN2018/096398, filed on Jul. 20, 2018, which claims the priority benefits of China Application No. 201810146715.6, filed on Feb. 12, 2018 and Chinese application no. 201910036674.X, filed on Jan. 15, 2019. The entirety of each of the above-mentioned patent applications is hereby incorporated by reference herein and made a part of this specification.

The instant application contains a Sequencing Listing which has been submitted electronically in ASCII text file and is hereby incorporated by reference in its entirety. Said ASCII copy, created on Feb. 1, 2023, is named 092569usf-DIV-sequencing list and is 7,615 bytes in size.

BACKGROUND

Technical Field

The present invention belongs to the field of biomedical technologies, and more particularly, relates to use of piRNA-54265 in diagnosis, treatment, and prognostic evaluation of colorectal cancer.

Description of Related Art

Colorectal cancer is a common gastrointestinal tumor worldwide, ranking high among various malignant tumors, and is one of the leading causes of cancer-related death around the world. It is clinically difficult to cure advanced colorectal cancer but not colorectal cancer at early stage. Therefore, early detection and diagnosis of colorectal cancer is of great significance for improving the curative effect and decreasing the morbidity. Colonoscopy is an important means for early diagnosis of colorectal cancer and has high accuracy, but it is an examination method causing wounds and is difficult to apply in the general population census due to high economic costs, requirements on operators and equipment and poor compliance of persons to do the examination. In addition, there are some early screening and companion diagnostic methods, but their sensitivity and specificity are poor. Therefore, it is of great demand and significance to develop and establish a less economical cost, technically simple, but sensitive and specific biomarker for early screening and diagnosis of colorectal cancer.

Meanwhile, chemotherapy for colorectal cancer is also plagued by drug resistance in tumor. According to the estimation of American Cancer Society, more than 90% of cancer patients die from some degrees of drug resistance, and the drug resistance in tumor has become the key factor for whether or not tumor chemotherapy is successful. There are significant individual differences in the effects of chemotherapy, but the mechanism is unclear and basically there are currently no biomarkers for predicting curative effect. In addition, there is a huge individual difference in the prognosis of colorectal cancer patients, and there is currently no indicator for evaluating prognosis. Therefore, elucidation and development of biomarkers for colorectal cancer curative effect and prognosis assessment are essential for precise treatment. Another important issue for colorectal cancer is the judgment of prognosis for patient treatment and the selection of right treatment solutions.

Therefore, the development of early screening, early diagnosis, treatment and prognosis of colorectal cancer, as well as therapeutic targets and related technologies are urgently needed, and have important significance and application prospects.

SUMMARY

The technical problem to be solved by the present invention is to overcome the defects and deficiencies of the existing diagnosis and treatment techniques for colorectal cancer, and to provide a new colorectal cancer diagnostic marker piRNA-54265 (PIWI-interacting RNA54265), which can be used for early diagnosis and early screening, and can specifically indicate the chemosensitivity and prognosis of a colorectal cancer patient, which is helpful for individualization and precision of clinical treatments; and can further be used as a therapeutic target for colorectal cancer and used for preparing a therapeutic drug for colorectal cancer. Further, the present invention also constructs a kit for early screening, diagnosis, curative efficacy monitoring and prognostic evaluation of colorectal cancer with the marker piRNA-54265 as a target.

An objective of the present invention is to provide a marker piRNA-54265 capable of being used for diagnosis and/or treatment of colorectal cancer.

Another objective of the present invention is to provide use of the marker piRNA-54265 in early screening, diagnosis, curative efficacy monitoring and prognostic evaluation of colorectal cancer.

One another objective of the present invention is to provide piRNA-54265 detection primer sets and kit for early screening, diagnosis, curative efficacy monitoring and/or prognostic evaluation of colorectal cancer.

The above-mentioned objectives of the present invention are achieved by the following technical solutions.

Upon research findings of the present invention: there are statistically significant differences in expression of the piRNA-54265 in colorectal cancer and para-carcinoma tissues, and the piRNA-54265 is highly expressed in cancer tissues. The expression level of the piRNA-54265 in the cancer tissues is related to the survival prognosis of the colorectal cancer patients, and the colorectal cancer patients with high level of piR-54365 has poorer prognosis. The piRNA-54265 can be detected in serums of the colorectal cancer patients, and the content of the piRNA-54265 in the serums is positively correlated with the content of the piRNA-54265 in the cancer tissues, and patients with high content have short survival time. Besides, the content of the serum piR-54265 in normal people is significantly lower than the colorectal cancer patient, and thus it is easy to distinguish. With piRNA-54265 knockdown, the abilities of proliferation, migration and invasion of colorectal cancer cells are significantly weakened, and the growth and metastasis of xenograft tumors in nude mice transplanted with colorectal cancer cells can also be significantly inhibited. When perturbing the expression level of the piRNA-54265, the colorectal cancer cells show a certain degree of enhancement of chemosensitivity; and the patients with high-expressed piRNA-54265 has poor short-term efficacy of chemotherapy. Moreover, the serum piR-54265 level can effectively predict the onset of colorectal cancer, and the serum piR-54265 can be found elevated for up to 3 years before the diagnosis of cancer. Early screening and early diagnosis of colorectal cancer can be conducted in general population with serum piR-54265 detection. Therefore, the piRNA-54265 can be used as a biomarker for early screening, diagnosis, efficacy evaluation and prognosis judgment of colorectal cancer.

Therefore, all the following use shall fall within the scope of protection of the present invention:

Use of the piRNA-54265 as a marker for diagnosis of colorectal cancer. The diagnosis includes early diagnosis and early screening.

Use of the piRNA-54265 as a prognostic evaluation marker for colorectal cancer.

Use of the piRNA-54265 as a chemosensitivity evaluation marker of a colorectal cancer patient.

Preferably, the piRNA-54265 refers to piRNA-54265 in serum or plasma, which can be easily detected by a blood specimen.

Use of the piRNA-54265 as a therapeutic target for colorectal cancer.

Use of the piRNA-54265 in making therapeutic agents or drugs for colorectal cancer.

Use of an inhibitor or a knockout reagent of the piRNA-54265 as a therapeutic drug for colorectal cancer.

Use of the inhibitor or the knockout reagent of the piRNA-54265 as an ancillary drug for improving the chemotherapeutic efficacy of colorectal cancer.

Preferably, the above-mentioned drug is a drug capable of inhibiting proliferation, invasion and/or metastasis of colorectal cancer cells.

In addition, when the piR-54265 is used as an inhibitor, an effective sequence is a reverse complementary sequence of an original sequence. Therefore, any form of modification taking the sequence as a basis or as an active ingredient shall be protected, i.e., a piRNA-54265 capable of being used for diagnosis and/or treatment of colorectal cancer shall also fall within the scope of protection of the present invention, and is specifically selected from one of molecules (1) to (6) as follows:

(1) SEQ ID NO:29: tggaggtgatgaactgtctgagcctgacc, (2) SEQ ID NO:30: UGGAGGUGAUGAACUGU-CUGAGCCUGACC, (3) SEQ ID NO:31: GGUCAGGCUCAGACAGUU-CAUCACCUCCA, (4) a piR-54265 variant and a piR-54265 derivative modified from the molecule shown in (1), (2) or (3) with a same function;

Manner of modification including but not limited to: methylated modification, hydrocarbyl modification, galactosylated modification (such as 2-methoxy-glycosyl modification, hydrocarbyl-glycosyl modification, sugar-ring modification, etc.), nucleination modification, peptide modification, lipid modification, halogen modification, nucleic acid modification (such as "TT" modification), or the like;

(5) a piR-54265 polynucleotide construct capable of affecting transcription of a corresponding genome after being introduced, thereby endogenously regulating the amount of the piR-54265; and (6) an expression vector containing the polynucleotide construct of (5).

The piRNA-54265 complementary sequence provided according to the present invention, can be introduced and processed into a polynucleotide construct which can affect the expression of the corresponding piR-54265, and the polynucleotide construct is capable of down-regulating the amount of the corresponding piRNA in vivo. The polynucleotide construct containing the piRNA-54265 complementary sequence can also be inserted into a cellular genome so as to continuously generate a transcription product that can specifically inhibit or degrade the piRNA.

Typically, the polynucleotide construct can be located on an expression vector. Accordingly, the present invention further includes a vector including the piRNA, or the polynucleotide construct. Usually, the expression vector further contains a promoter, an origin of replication, and/or a marker gene and the like. Methods well known to those skilled in the art can be used to construct the expression vector required for the present invention. These methods include DNA recombination techniques in vitro, DNA synthesis techniques, recombination techniques in vivo, and the like. The expression vector preferably includes one or more selectable marker genes to provide phenotypic character for selection of transformed host cells, such as kalamycin, gentamicin, hygromycin, ampicillin resistance, etc. Moreover, the polynucleotide construct is not limited to other genome or transcriptome regulating methods in the art, such as CRISPR-Cas9.

In addition, based on the above studies, the piR-54265 related to the present invention can be used as a specific molecular marker for cancer incidence or risk prediction, early screening, early diagnosis, therapeutic sensitivity, and prognostic evaluation of cancer, and a therapeutic target for cancer.

Therefore, the present invention provides a method for diagnosing/screening colorectal cancer, including detecting the expression level of piRNA-54265 in a specimen under test (such as tissue, serum, plasma and even other types of specimens like urine and saliva), and judging whether the specimen to be detected suffers from the colorectal cancer or has a risk of suffering from the colorectal cancer according to the expression level of the piRNA-54265.

A method for evaluating chemosensitivity of a colorectal cancer patient includes detecting the expression level of piRNA-54265 in a specimen under test (such as tissue, serum, plasma or other types of specimens), and evaluating the chemosensitivity of the patient according to the expression level of the piRNA-54265.

A method for evaluating prognosis of a colorectal cancer patient is characterized by detecting the expression level of piRNA-54265 in a specimen under test (such as tissue, serum, plasma or other types of specimens), and evaluating the prognosis of the patient according to the expression level of the piRNA-54265.

Methods for detecting the expression level of the piRNA-54265 are not strictly limited, and all the methods in the art capable of achieving the detection objects can be used and shall fall within the scope of protection of the present invention.

Specifically, the methods for detecting the expression level of the piRNA-54265 include, but are not limited to molecular detection techniques, and all the methods and use involving direct and/or indirect, qualitative and/or quantitative detection of the piR-54265 shall fall within the scope of protection of the present invention, including specific primers and/or probes for detecting piR-54265.

The present invention further provides a method for treating colorectal cancer, including performing gene therapy with piRNA-54265 as a target to inhibit or silence expression of the piRNA-54265, so as to realize a purpose of treating and assisting in treating colorectal cancer.

Methods for performing gene therapy on the colorectal cancer with the piRNA-54265 as the target are not strictly limited, and all the methods in the art capable of achieving the gene therapy object can be used and shall fall within the scope of protection of the present invention.

In addition, as an alternative implementation, the present invention further provides a specific solution for detecting piRNA-54265, i.e., quantitative PCR detection, which provides a specific primer design pattern for piRNA-54265 and constructs a kit. The specific solution is as follows:

a piRNA-54265 detection kit for early screening, diagnosis, curative efficacy monitoring and prognosis evaluation of colorectal cancer includes primer set for specifically detecting piRNA-54265, wherein the primers are a quantitative PCR primer pair which includes a forward primer and a reverse primer, and the forward primer is designed based on the sequence of the piRNA-54265 (which changes U in the RNA sequence of the piRNA-54265 to T), and sequentially includes an amount of bases from the 5'- of the sequence, and shall include the first five bases "TGGAG" at least.

As a preferred selectable solution, the primer pair can be a piRNA-54265 stem-loop PCR primer pair, or a piRNA-54265 PolyA tailed PCR primer pair.

Preferably, the piRNA-54265 stem-loop PCR primer pair is shown as SEQ ID NO:8/9, SEQ ID NO:10/9, SEQ ID NO:11/9, SEQ ID NO:12/13, SEQ ID NO:14/13, SEQ ID NO:15/13, SEQ ID NO:16/13, SEQ ID NO:17/13, SEQ ID NO:18/13, SEQ ID NO:19/13 or SEQ ID NO:20/13.

Preferably, the piRNA-54265 PolyA tailed PCR primer pair is shown as SEQ ID NO:8/21, SEQ ID NO:10/21, SEQ ID NO:11/22, SEQ ID NO:12/22, SEQ ID NO:14/23, SEQ ID NO:15/22, SEQ ID NO:16/22, SEQ ID NO:17/22, SEQ ID NO:18/22, SEQ ID NO:19/22 or SEQ ID NO:20/22.

Most preferably, the forward primer and the reverse primer of the stem-loop primer pair are respectively shown as SEQ ID NO:26 and SEQ ID NO:9.

Most preferably, the forward primer and the reverse primer of the PolyA tailed primer pair are respectively shown as SEQ ID NO:26 and SEQ ID NO:22.

Moreover, the kit further includes a probe used cooperatively with the primers.

Preferably, the probe used cooperatively with the stem-loop primer is shown as SEQ ID NO:27.

In addition, the kit further includes an RNA reverse transcription primer.

Preferably, the piRNA-54265 stem-loop reverse transcription primer has a sequence shown as SEQ ID NO:2.

Preferably, the piRNA-54265 PolyA tailed reverse transcription primer has a sequence shown as SEQ ID NO:3-5.

In addition, preferably, when using the kit of the present invention, if a real-time fluorescent quantitative PCR is adopted, a reaction system thereof is as shown in Table 13 and Table 14, and a reaction procedure is as shown in Table 15. If a droplet digital PCR is adopted, a reaction system thereof is as shown in Table 16, and a reaction procedure is as shown in Table 17.

The present invention has the following beneficial effects.

It is found and disclosed by the present invention for the first time that there are statistically significant differences in expression of the piRNA-54265 in colorectal cancer and para-carcinoma tissues, and the piRNA-54265 is high-expressed in cancer tissues. Therefore, the piRNA-54265 can be used as a diagnostic marker for colorectal cancer and used for diagnosing colorectal cancer.

Meanwhile, it is also found by the present invention that the expression level of the piRNA-54265 in the cancer tissues is related to the survival prognosis of the colorectal cancer patients, and the colorectal cancer patient with high expression level of piR-54265 has poor prognosis, so the piRNA-54265 can be used as a prognostic evaluation marker for colorectal cancer and used for prognostic evaluation of colorectal cancer.

Furthermore, it is also founded by the present invention that the expression of the piRNA-54265 can be detected in serums of the colorectal cancer patients, and the expression level of the piRNA-54265 in the serums is positively correlated with the expression level of the piRNA-54265 in the cancer tissues, and is related to the survival prognosis of the patients. In addition, the expression level of the serum piR-54265 of normal people is low, which is significantly different and well differentiated in comparison with the expression level of the serum piR-54265s of the colorectal cancer patients. Moreover, the serum piR-54265 level can effectively predict the onset of colorectal cancer, and the serum piR-54265 can be found elevated for up to 3 years before the diagnosis of cancer. Therefore, the piR-54265 can not only be easily detected in a blood specimen, but also be used for performing early diagnosis or preliminary screening. Moreover, it is also founded by the present invention that with piRNA-54265 knockdown, the abilities of proliferation, migration and invasion of colorectal cancer cells are significantly weakened, and the growth and metastasis of xenograft tumors in nude mice transplanted with colorectal cancer cells can also be significantly inhibited. Therefore, the piRNA-54265 can be used as a therapeutic target for colorectal cancer and used for treating colorectal cancer. Finally, it is also found by the present invention that when increasing or decreasing the expression level of the piRNA-54265, the colorectal cancer cells show a certain degree of reduction or enhancement of chemosensitivity; and the patients with high-expressed piRNA-54265 has poor short-term efficacy of chemotherapy. Therefore, the piRNA-54265 can be used as adjunctive therapy for chemotherapy.

The comprehensive results sufficiently show that the piR-54265 is an important potential therapeutic target for cancer and a molecular marker for cancer screening, diagnosis and treatment, but is not limited to serum, plasma or tissue, and is not limited to colorectal cancer. The piR-54265 is expected to be developed, transformed and applied in clinical work, and the effects thereof can be further explored and analyzed in various systemic tumors.

Based on the above research results, the present invention further provides a piRNA-54265 detection kit which can be used for early screening, diagnosis, efficacy monitoring and prognosis evaluation of colorectal cancer. The present invention originally provides a specific primer design pattern for the piRNA-54265, and verifies that both the amplification efficiency and specificity of the primers designed thereof are excellent. The kit provides a complete process from RNA purification of specimen to the expression level detection of the target piRNA 54265. The process is already optimized for easy and efficient operation. Moreover, when the kit is in use, a specimen to be detected is suitable for tissues, cells, cell supernatant and body fluids such as serum (plasma), urine, saliva, and other types of specimens with rare RNA, and the required specimen amount is less than that of the same type of kits in the market. Meanwhile, two optional expression detection methods including real-time fluorescent quantitative PCR and absolute quantitative droplet digital PCR are provided, so the application range is wide.

BRIEF DESCRIPTION OF THE DRAWINGS

FIGS. 1a~1d show that TCGA data analysis and tissue specimens of patients detection indicates the increased expression level of piR-54265 in colorectal cancer.

FIGS. 3a~3d show that high expression level of the piR-54265 in serum associates with poor survival prognosis in colorectal cancer patients.

FIGS. 4a~4d show the effects of piR-54265 expression on the capability of proliferation, colony formation, migration, invasion and anti-apoptosis in colorectal cancer cells.

FIGS. 6a~6f show that piR-54265 bindsPIWIL2 promoting the activation of STAT3 and downstream signaling pathway.

FIGS. 7a~7b show effects of piR-54265 on sensitivity of colorectal cancer cells and mouse subcutaneous xenograft tumors to chemotherapeutic agents.

FIGS. 8a~8g show that a specific piR-54265 inhibitor inhibits the growth and metastasis of mouse subcutaneous xenografts.

FIGS. 9a~9c show that high level of piR-54265 associates with a poor short-term efficacy of chemotherapy in colorectal cancer patients.

FIG. 10 shows the piR-54265 level of the baseline serum in the normal people and people whom found onset of colorectal cancer in the later follow-up and grouped by the diagnosed time from blood sampling.

FIG. 11 shows schematic diagram of design modes for PCR primers of a stem-loop primer method and a PolyA tailed method.

FIG. 16a shows amplification curves of the serum piRNA-54265 as well as external reference cel-miR-39 of the samples in patients before and after operation; and FIG. 16b shows the corresponding melting curves.

DESCRIPTION OF THE EMBODIMENTS

Figure 2:
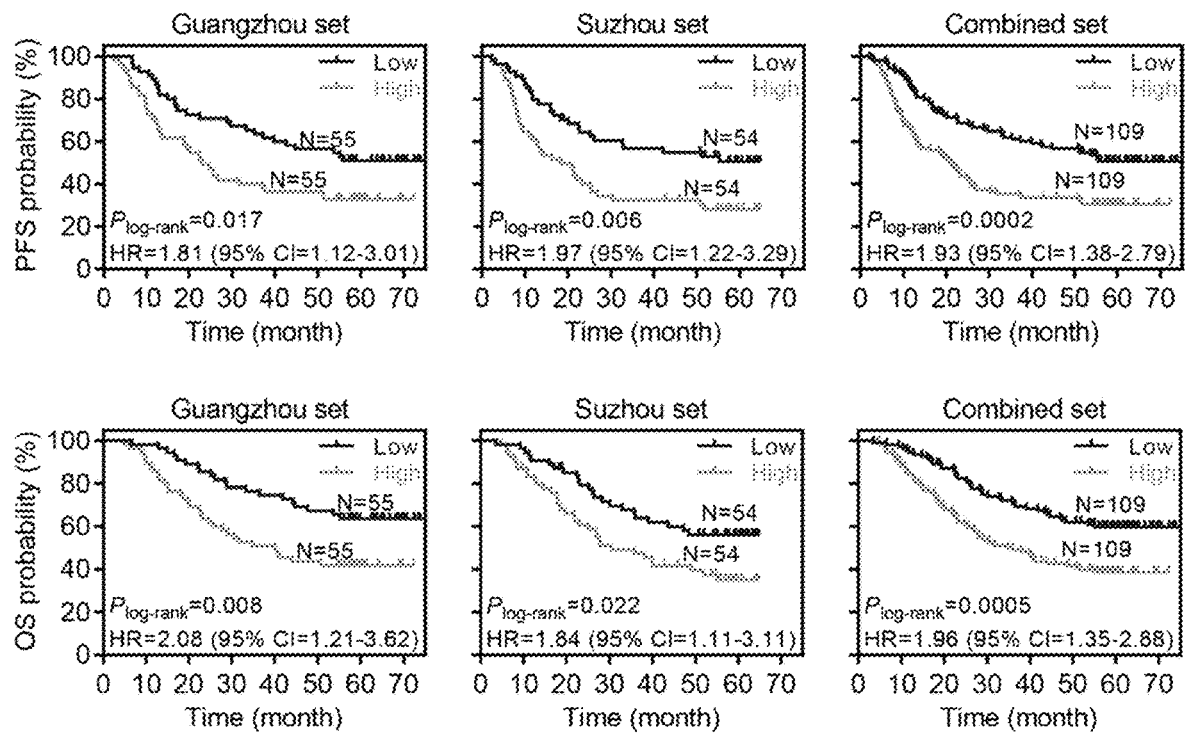
FIG. 2 shows that high expression level of the piR-54265 in cancer tissues associates with poor survival prognosis in colorectal cancer patients.

The present invention is further described below with reference to the accompanying drawings and specific embodiments, but the embodiments are not intended to limit the present invention. Those of ordinary skills in the art should understand that modifications or equivalent substitutions can be made on the technical solutions of the present invention without departing from the spirit and scope of the technical solutions of the present invention. Any other changes, modifications, substitutions, combinations, and simplifications made without departing from the spirit and scope of the present invention are intended to be equivalents and are included in the protection scope of the present invention.

Unless otherwise indicated, the reagents, methods, and devices employed in the present invention are routine reagents, methods, and devices in the art. The reagents and materials used in the following embodiments are commercially available unless otherwise stated. Experimental methods that do not specify the specific conditions are usually in accordance with conventional conditions, such as those described in textbooks and experimental guides, or in accordance with the conditions recommended by the manufacturers.

Embodiment 1 TCGA Data Analysis and Tissue Specimens of Patients Detection Indicates the Increased Expression Level of a piR-54265 in Colorectal Cancer 1. Experimental Method:

TCGA and GEO expression profile data were extracted and analyzed to obtain 20 top high-expressed piRNAs in colorectal cancer. Specific primers were designed for the top 20 piRNAs, and then expression quantitation by qPCR was performed in 110 tumor tissue and paired non-tumor tissue specimens of colorectal cancer patients from Guangzhou. The expression level of the identified piR-54265 was verified in another 108 tumor tissue and paired non-tumor tissue specimens of colorectal cancer patients from Suzhou. Bioinformatics analysis of the gene copy number variation and DNA methylation modification of piRNA-54265 was performed According to the COAD data in TCGA database.

2. Experimental Results:

As shown in FIGS. 1a and 1b, only the expressions of the piRNA-54265 in the colorectal cancer tissue and the paired para-carcinoma tissue have significant statistical differences, the piRNA-54265 is high-expressed in the cancer tissue, and the same results are obtained from the specimens of two clinical centers (Guangzhou and Suzhou).

The piRNA-54265 (Accession: DQ587153) is a mature body formed by a precursor snoRNA57 thereof after intracellular processing, with a sequence of 29 nucleotides in length and a genome located at CHR 20: 2637585-2637613; and a sequence thereof is as follows:

```
SEQ ID NO. 29:
tggaggtgatgaactgtctgagcctgacc,
or

SEQ ID NO. 30:
UGGAG GUGAU GAACU GUCUG AGCCU GACC.
```

An effective sequence of the piRNA-54265, i.e., a reverse complementary sequence of the original sequence, is:

```
SEQ ID NO. 31:
5'-GGUCAGGCUCAGACAGUUCAUCACCUCCA-3'.
```

As shown in FIGS. 1c and 1d, DNA methylation and SCNA results suggested that the piRNA-54265 had reduced DNA methylation and increased gene copy number amplification in colorectal cancer patients, and the difference was statistically significant compared with a normal set. This further explained the increased expression of the piRNA-54265 in colorectal cancer patients from the genomic level.

Embodiment 2 High Expression Level of the piR-54265 in Cancer Tissues Associates with Poor Survival Prognosis in Colorectal Cancer Patients 1. Experimental Method:

SPSS (19.0) was used to analyze the expression of the piR-54265 in cancer tissues and the prognosis of colorectal cancer patients (such as the above-mentioned 110 colorectal cancer patients with postoperative chemotherapy from Guangzhou and 108 colorectal cancer patients with postoperative chemotherapy from Suzhou).

2. Experimental Results:

The expression level of the piR-54265 in cancer tissues was related to the survival prognosis of the colorectal cancer patients. The high-expressed piR-54265 was associated with poor prognosis of the colorectal cancer patients, having both shorter 5-year overall survival and 5-year progression-free survival. The results were consistent in the two sample sets, Guangzhou and Suzhou (as shown in FIG. 2).

Embodiment 3 High Expression Level of the piR-54265 in Serum Associates with Poor Survival Prognosis of in Colorectal Cancer Patients 1. Experimental Method:

four serum specimens were randomly selected from the samples of colorectal cancer cases previously mentioned for Northern Blot to directly determine the presence or absence of piR-54265 in serum; then, RNA extraction and piR-54265 expression detection by RT-qPCR were performed on all serum specimens, and the correlation between the serum piR-54265 and the piR-54265 level in the cancer tissues was analyzed. Survival analysis was performed on the serum piR-54265 level and the prognosis of the corresponding patients. RNA was extracted from 111 serum specimens of normal people followed by piR-54265 expression detection via RT-qPCR and unpaired Student's t-test statistical analysis was performed to compare the serum piR-54265 levels of normal people and the colorectal cancer patients.

2. Experimental Results:

As shown in FIG. 3a, the piRNA-54265 could be detected in the serum of the colorectal cancer patients. In FIG. 3b and FIG. 3c, the expression level of the piRNA-54265 in the serums of the patients was positively correlated with the expression level of the piRNA-54265 in the cancer tissues, and was negatively related to the survival prognosis of the patients. In FIG. 3d, the expression level of the serum piR-54265 in the colorectal cancer patients was higher than that in the normal people, and the difference was statistically significant. The above results indicate that the expression level of the serum piR-54265 has the potential as an important marker for early diagnosis and prognosis prediction of colorectal cancer.

Embodiment 4 Effects of piR-54265 Expression on the Capability of Proliferation, Colony Formation, Migration, Invasion and Anti-Apoptosis in Colorectal Cancer Cells 1. Experimental Method:

Colorectal cancer cell lines HCT116 and LoVo with stably overexpressed and knockdown piR-54265 were successfully constructed, and then colony formation, cell migration or invasion, CCK-8 cell viability detection, cell apoptosis by Annexin-V/PI flow cytometry and cell cycle analysis by flow cytometry were performed on these cells.

2. Experimental Results:

As shown in FIG. 4, functional verification of the piRNA-54265 was performed in two colorectal cancer cell lines in vitro, and the results demonstrated that: compared with the control, overexpression of the piRNA-54265 significantly enhanced the ability of proliferation (FIG. 4a), colony formation (FIG. 4b), anti-apoptosis (FIG. 4c) as well as invasion and migration (FIG. 4d) of the colorectal cancer cells. On the contrary, after knocking down the piRNA-54265, both the proliferation and invasion abilities of the colorectal cancer cells were significantly decreased. perturbing the expression of the piR-54265 did not affect the progression of cell cycle (not shown).

Embodiment 5 Effects of piR-54265 Expression on Subcutaneous Xenograft Growth and Metastasis of CRC Cells in Nude Mice 1. Experimental Method:

Colorectal cancer cell lines with stably overexpressed (OE) or knockdown (KD) piR-54265 were inoculated subcutaneously into nude mice to format subcutaneous xenograft tumors. The volume of the subcutaneous xenograft tumors was recorded weekly after successful modeling. The piR-54265 OE and KD cell lines were further constructed to co-express luciferase (Luc). Luc cells were injected into the nude mice via tail vein to establish metastatic xenograft tumors. After successful modeling, an In-vitro Imaging System (IVIS) was used to periodically detect Luc photon values in the nude mice to monitor the progress of the metastasis.

Figure 5A:
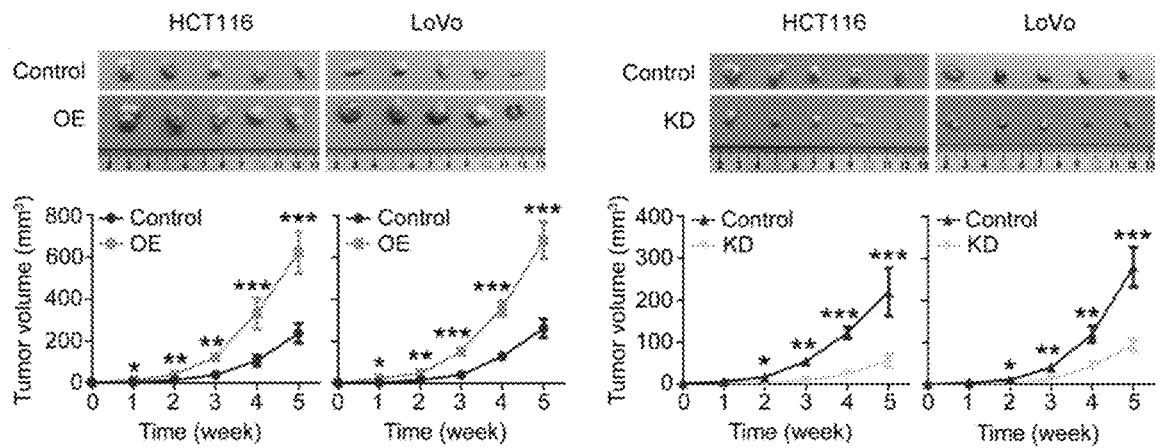
FIGS. 5a~5b show the effects of piR-54265 expression on subcutaneous xenograft growth and metastasis of CRC cells in nude mice.
Figure 5B:
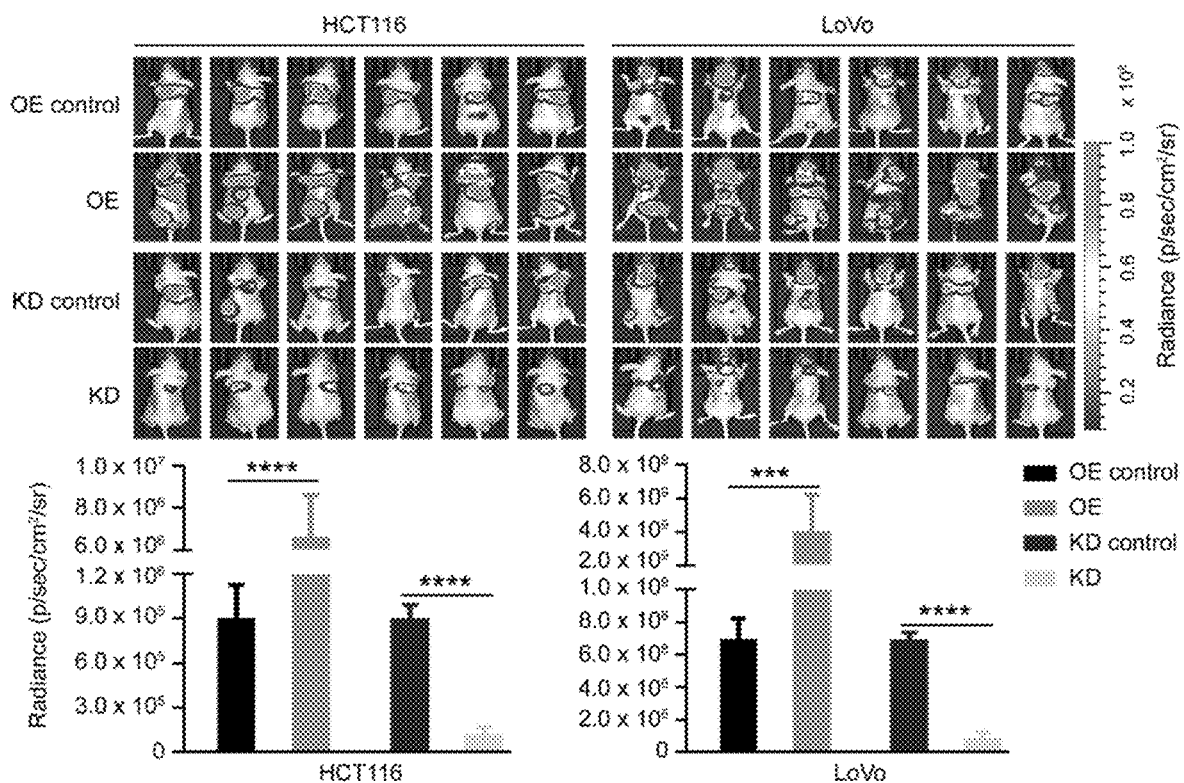
Figure 12A:
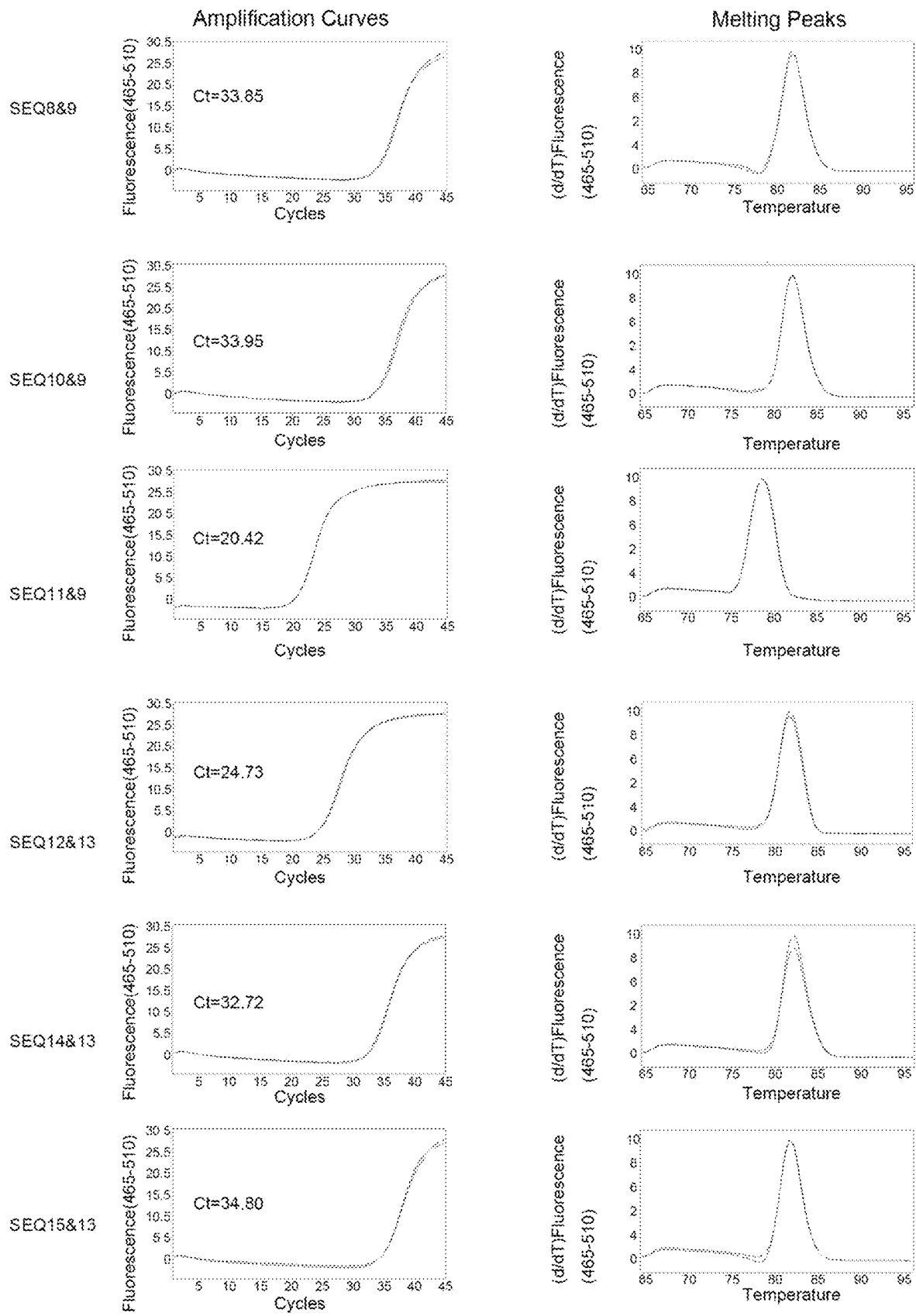
FIGS. 12a~12b show amplification curves and melting curves of 11 pairs of primers of the stem-loop method.
Figure 12B:
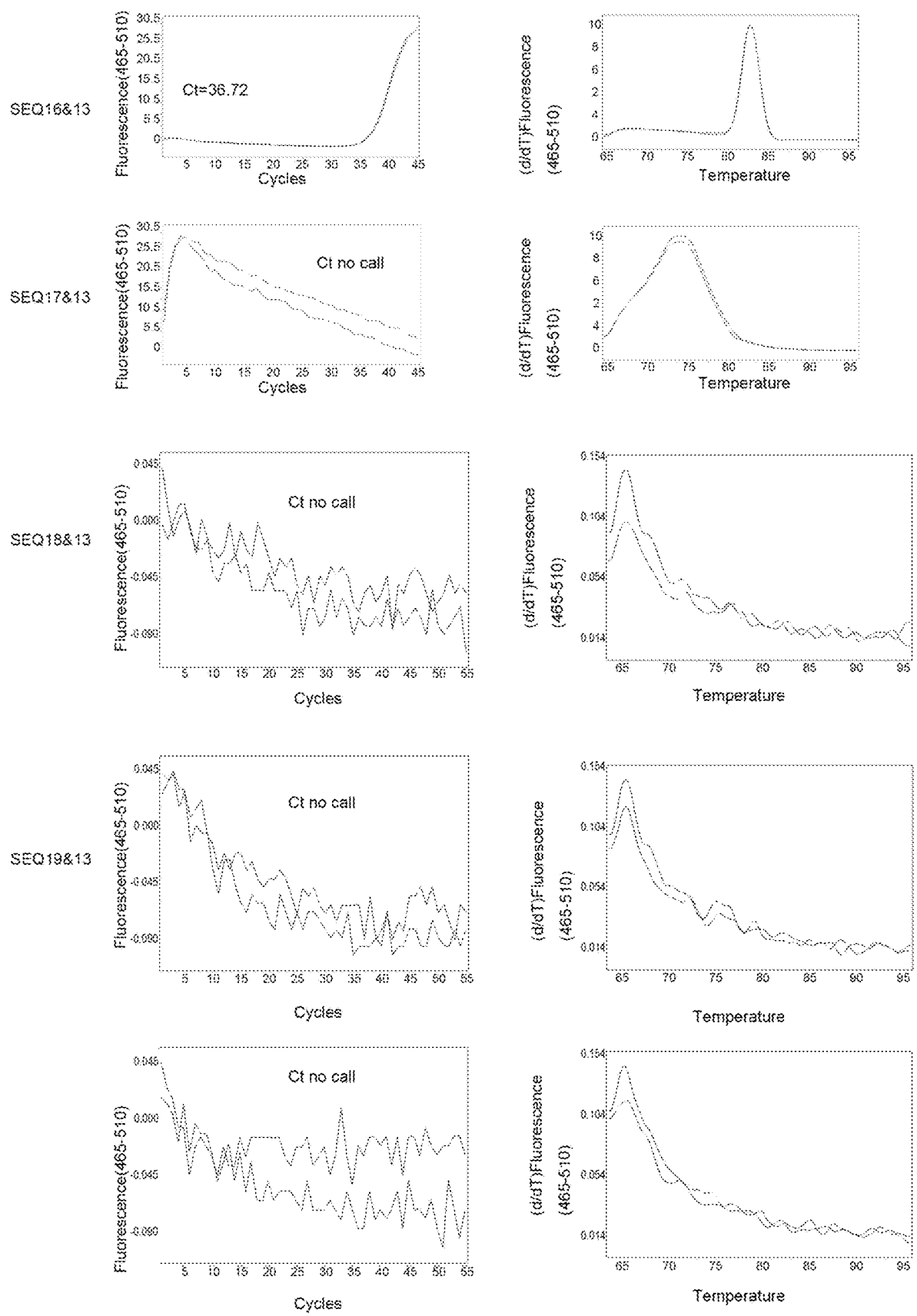
Figure 13A:
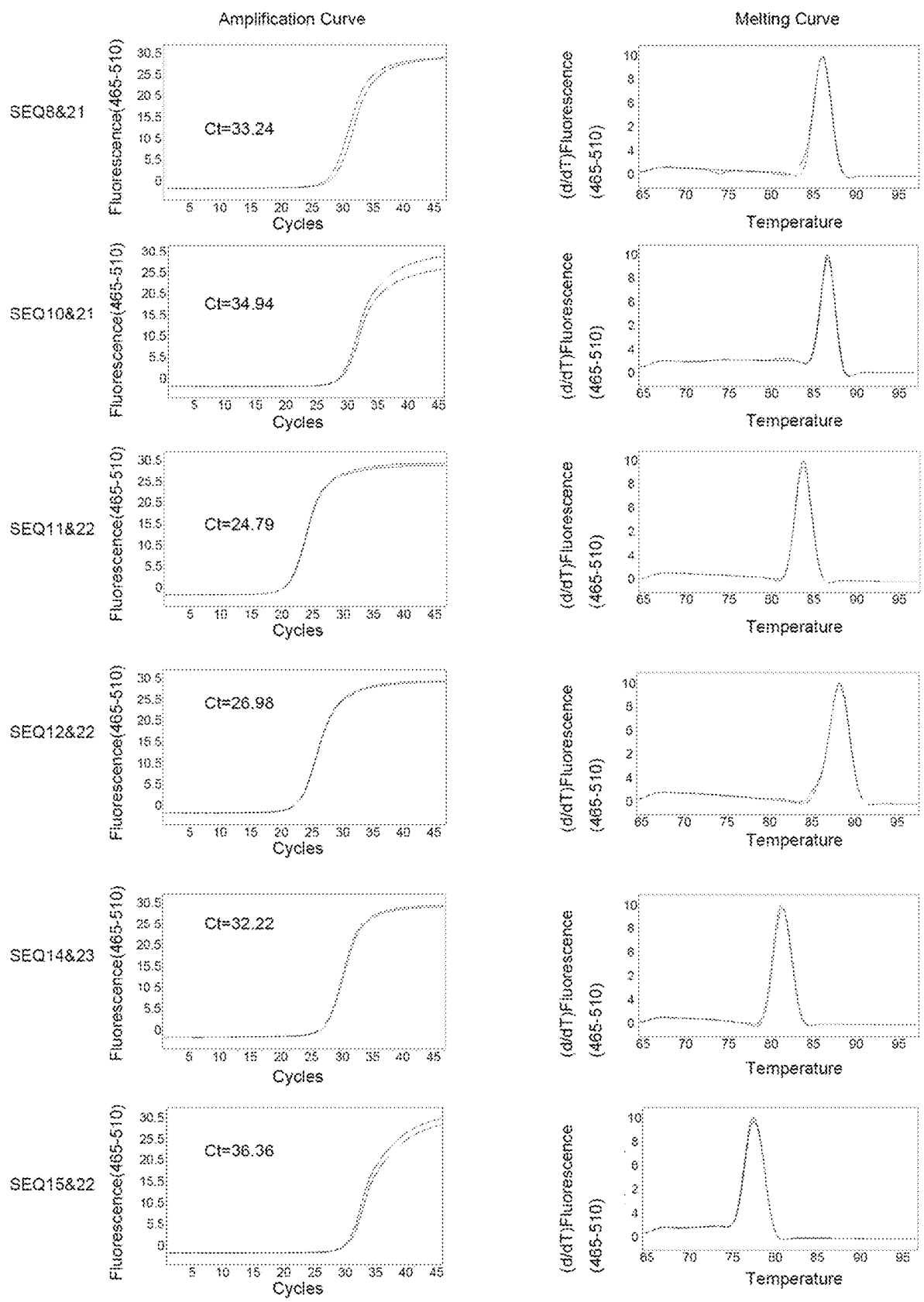
FIGS. 13a~13b show amplification curves and melting curves of 11 pairs of primers of the PolyA tailed method.
Figure 13B:
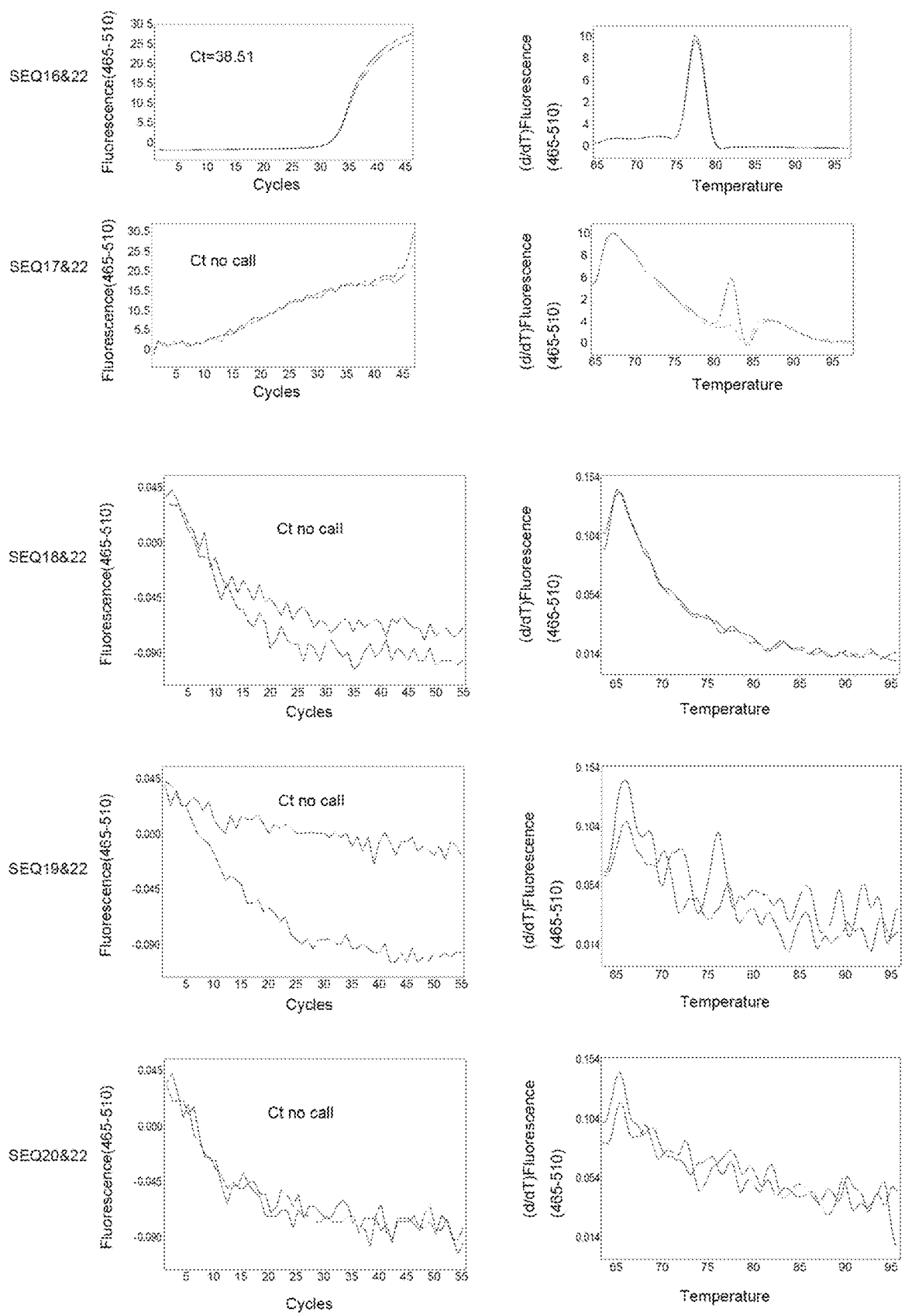

2. Experimental Results:

As shown in FIGS. 5a-5b, the results of the animal experiments demonstrated that, the overexpression of the piRNA-54265 could promote the growth of the subcutaneous xenograft tumors as well as distant metastasis and colonization of the cancer cells in the nude mice; the results were reversed while the piRNA-54265 was knockdown.

Embodiment 6 Study on the Molecular Mechanism of piR-54265 in Promoting Generation and Development of Colorectal Cancer 1. Experimental Method:

In an RNA immunoprecipitation (RIP) experiment, an antibody of a protein in PIWI protein family was used to perform immunoprecipitation (IP) in total RNA of colorectal cancer cells, and RT-qPCR was then performed after the PIWI protein precipitated RNAs were eluted. In a Pull Down experiment, the synthesized biotin-labeled piR-54265 was incubated with streptomycin magnetic beads and then incubated in fresh protein lysates of HCT116 and LoVo cells respectively, and then Western Blot was performed after the piR-54265-pulldownproteins were eluted. Western Blot was performed to analyze the changes of the expression of the downstream proteins when perturbing the expression of the piR-54265. In a Co-IP experiment, fresh protein lysates of cells with perturbed piR-54265 were incubated with PIWIL2 or STAT3 antibody respectively followed by Western Blot to analyze the combination of PIWIL2 and STAT3.

2. Experimental Results:

FIG. 6a and FIG. 6b endogenously and exogenously proved that the piR-54265 can specifically bind with the PIWIL2 protein. Perturbing the expression level of the piR-54265 do not obviously change the levels of STAT3 and SRC proteins but the phosphorylated STAT3 (p-STAT3). The expression of the p-STAT3 protein was up-regulated when overexpressing the piR-54265 (FIG. 6c).

Furthermore, the Co-IP experiment demonstrated that the PIWIL2, STAT3 and SRC protein could combine with each other, and the overexpression or knockdown of the piR-54265 could increase or reduce their combination (FIG. 6d).

Western blot analysis verified that, piR-54265 interacts with STAT3 and regulates a series of apoptosis and metastasis related downstream molecules of STAT3 (FIG. 6e).

In this study, a series of molecular biology experiments were used to elucidate a cancer-promoting mechanism of the piRNA-54265 (signaling pathway and molecular mechanism shown in FIG. 6f), which could bind PIWIL2, and then promote the activation of STAT3 and its downstream anti-apoptosis and metastasis signaling, thus promoting the growth and metastasis of colorectal cancer.

Embodiment 7 Effects of piR-54265 on Drug Sensitivity of Colorectal Cancer Cells 1. Experimental Method:

$IC_{50}$ experiments with the first-line colorectal cancer chemotherapy drugs 5-FU and L-OHP were respectively performed on colorectal cancer cell lines with stably over-expressed or knockdown piR-54265. Subcutaneous xenograft tumors in nude mice were established using the stable cell lines mentioned above, and when a tumor volume reached 250 mm$^3$, treatment of intraperitoneal injection with 5-FU or L-OHP was started, and the change of the tumor volume was periodically measured.

2. Experimental Results: as shown in FIG. 7a, the changes of the $IC_{50}$ of the colorectal cells suggested that piRNA-54265 could affect the chemosensitivity of colorectal cancer cells. When overexpressing the piR-54265, the chemoresistance of the colorectal cancer cells to 5-FU and L-OHP could be enhanced, and the cell chemosensitivity was improved after knocking down the piR-54265. The results were consistent in the animal experiments (FIG. 7b): overexpression of the piR-54265 significantly reduced the efficacy of chemotherapy drugs on the subcutaneous xenograft tumors, while knockdown of piR-54265 significantly enhanced the chemosensitivity to the drugs and the xenograft tumors shrank remarkably.

Embodiment 8 Specific piR-54265 Inhibitor Inhibits the Growth and Metastasis of Mouse Subcutaneous Xenografts 1. Experimental Method:

Colorectal cancer cell lines with stably overexpressed or knockdown piR-54265 were inoculated subcutaneously into a nude mouse respectively to establish subcutaneous xenograft tumors. When the tumor volume reached 50 mm$^3$, a specific piR-54265 inhibitor was multi-pointedly injected into the tumors, and the tumor volume was monitored and recorded regularly (see FIG. 8a for specific operation time). The piR-54265 overexpressed (OE) or knockdown (KD) colorectal cancer cells co-expressing Luciferase were injected into the nude mice via tail vein to establish metastatic xenograft tumors, and the luminescence value was monitored by IVIS regularly. When the luminescence value reached $1 \times 10^6$ p/sec/cm$^2$/sr, the specific piR-54265 inhibitor was injected via tail vein or combined with chemotherapy drug 5-FU intraperitoneally injected periodically, and the progress of the metastasis was monitored by IVIS (see FIG. 8b for specific operation time).

2. Experimental Results:

The results were shown in FIGS. 8c to 8g. Using the specific piRNA-54265 inhibitor or combined with chemotherapy drug for tumor treatment in nude mice could effectively inhibit the growth of the subcutaneous and metastatic xenograft tumors, and significantly prolonged the overall survival time of the metastatic xenograft nude mice. Therefore, the specific piR-54265 inhibitor had a certain anti-cancer effect and could assist in improving curative effect of the chemotherapy drugs, and the piR-54265 inhibitor might probably become a new therapeutic target for colorectal cancer.

Embodiment 9 High Level of piR-54265 Associates with a Poor Short-Term Efficacy of Chemotherapy in Colorectal Cancer Patients 1. Experimental Method:

Serum specimens were collected before any treatment from colorectal cancer patients who received preoperative neoadjuvant chemotherapy in Guangzhou (215 cases, training set) and Beijing (102 cases, verification set). Total RNAs were extracted from the serum samples followed by RT-qPCR detection for piRNA-54265 expression. Then analyze the relationship between the piR-54265 expression of the patients and their curative efficacy after neoadjuvant chemotherapy, and ROC curve was performed to evaluate the efficacy of serum piR-54265 in predicting chemotherapeutic effect and obtain an optimal cutoff value.

2. Experimental Results:

In order to more directly investigate the relationship between the piRNA-54265 and chemotherapy, and eliminate the interference of many complicated factors i.e. operation, serum specimens were selected before treatment from colorectal cancer patients who received neoadjuvant therapy. As shown in FIG. 9a and FIG. 9b, patients with high-expressed piRNA-54265 in serum had poor short-term efficacy of chemotherapy; and the results in two sample sets were consistent. The ROC curve was constructed for the short-term efficacy of chemotherapy of patients based on the expression level of piR-54265 in serum, and the results were shown in FIG. 9c. In the training set, the expression level of the piR-54265 in serum could accurately reflect the efficacy of chemotherapy or chemosensitivity of the colorectal cancer patients (AUC=0.819, P<0.0001, Guangzhou), and the corresponding cutoff value of the ROC curve was 0.01227 (the sensitivity was 66.7%, and the specificity was 90.0%). The Cutoff value was used to model and simulate in the verification set, wherein the sensitivity was 53.3%, the specificity was 93.1%, AUC=0.808, and P<0.0001. Therefore, the piRNA-54265 would be a potential and promising specific molecular marker of colorectal cancer, which could be easily detected in blood specimen and specifically indicated the chemosensitivity and prognosis of the colorectal cancer patients, and the expression level of the piR-54265 in serum and the cutoff value would be helpful for more accurate individualized selection of clinical therapeutic regime and improvement of prognosis.

Embodiment 10 Prospective Nested Case-Control Study on the Efficacy of Baseline Serum piR-54265 Level in Early Screening for Colorectal Cancer in General Population 1. Experimental Method:

A total of 1160 baseline serum specimens were collected from 2008 to 2013 from normal people whom were followed-up for a long time to monitor and record the cancer status. Under the double-blind design, the expression of piR-54265 was absolutely quantitated in the 1160 serum specimens from the normal people by droplet digital PCR. After unblinding, statistical analysis was performed to investigate the efficacy of the baseline serumpiR-54265 level in predicting the risk of colorectal cancer of general people or recognizing colorectal cancer from general people in advance.

2. Experimental Results:

The results were shown in FIG. 10. The closer to the time of final diagnosis of colorectal cancer, the higher the expression level of the serum piR-54265 was. The serum piR-54265 could effectively predict the onset of colorectal cancer, and the serum piR-54265 could be detected sensitively high-expressed up to 3 years before the onset of cancer.

Therefore, the serum piR-54265 could be used for early screening and early diagnosis of colorectal cancer in general people, which could effectively predict the onset three years earlier.

In summary, the research results showed that: the high-expressed piRNA-54265 (piR-54265) in colorectal cancer tissues and serums/plasma promoted malignant growth and metastasis of colorectal cancer cells. The piR-54265 was closely related to the onset, prognosis and chemotherapeutic efficacy of the colorectal cancer, was a potential evaluation marker for early screening, early diagnosis, prognostic evaluation and chemosensitivity of the colorectal cancer, and was a potential therapeutic target for colorectal cancer. We further detected the serum piR-54265 levels in several common digestive system tumors, and the results showed the specificity and high expression of the serum piR-54265 in colorectal cancer. In a prospective study for screening colorectal cancer in a large cohort of general people, the results showed that the serum piR-54265 could effectively predict the onset of colorectal cancer, which was three years earlier than the diagnosed time.

The comprehensive results sufficiently showed that the piR-54265 was an important and potential therapeutic target for colorectal cancer and a molecular marker for screening, diagnosis and treatment of colorectal cancer, and was not limited to the type of specimen, serums, plasma or tissues, and was not limited to colorectal cancer either. The piR-54265 was expected to be developed, transformed and applied in clinical work, and the effects thereof could be further explored and analyzed in various systemic tumors.

Therefore, early screening, early diagnosis, as well as chemosensitivity and prognosis evaluation of the colorectal cancer could be performed by detecting the expression level of the piR-54265, and gene therapy for colorectal cancer could be performed using the piR-54265 as a target.

The following embodiments 11 to 15 present a solution suitable for detecting the expression level of the piR-54265, including design of detection primers, a detection method and construction of a detection kit, and evaluation of the kit.

Embodiment 11 piR-54265 Primer Design and Specific Design Model

Figure 11:
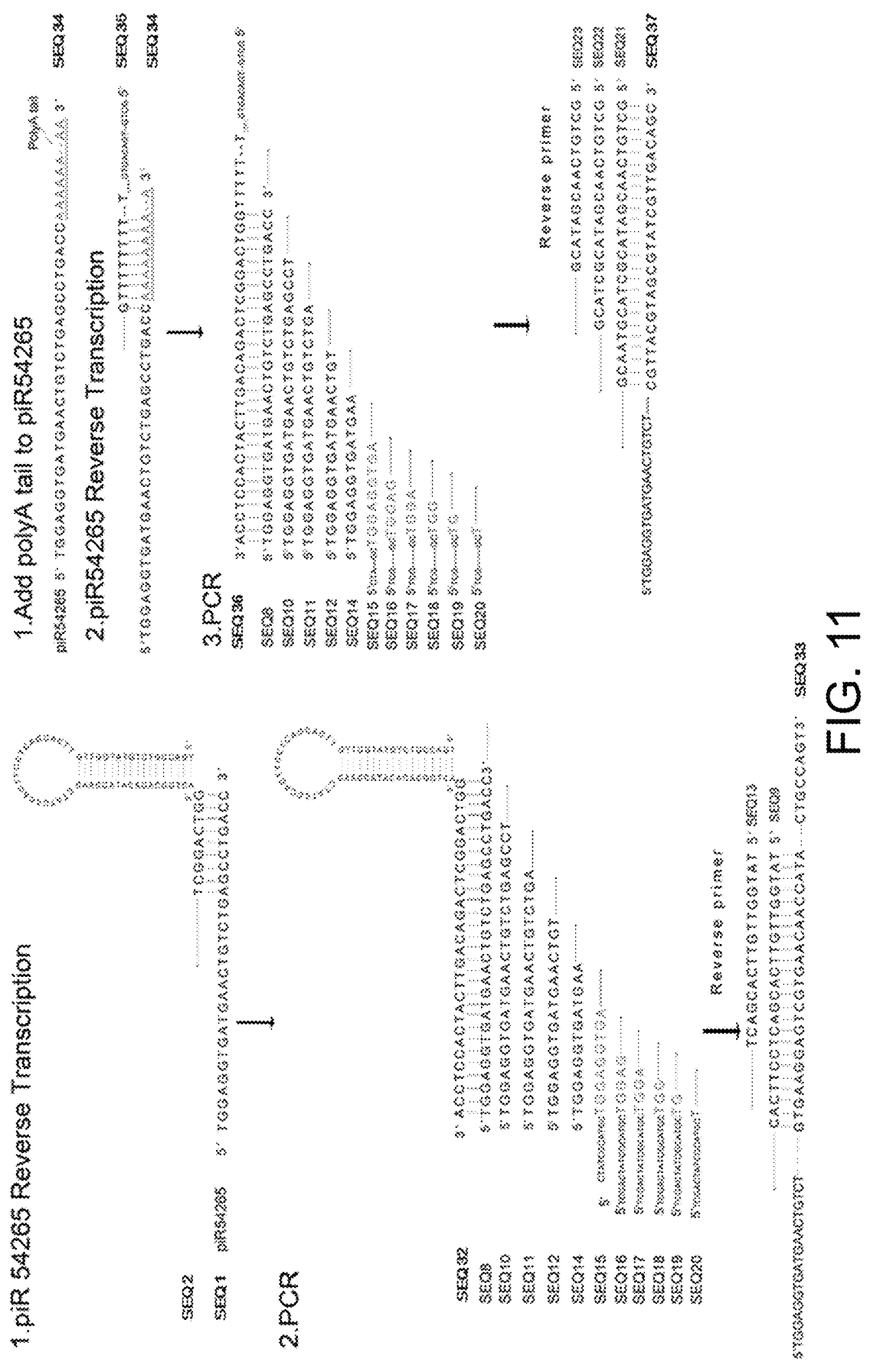

1. Reverse transcription primers (as shown in Table 1 and Table 2) were respectively designed by two small RNA reverse transcription methods including a stem-loop method and a PolyA tailed method, and PCR primers were designed accordingly so as to quantify the piRNA-54265. The specific design ideas were shown in FIG. 11 below.

Design principles for forward primers of the stem-loop method and the PolyA tailed method were similar. A forward primer is designed based on the sequence of the piRNA-54265 (which changes U in the RNA sequence of the piRNA-54265 to T), and sequentially includes an amount of bases from the 5'⁻ of the sequence, and shall include the first five bases "TGGAG" at least. In general, fluorescence quantitative PCR primers were 17 to 25 nt in length. Therefore, when the current primer was designed to be a full length of the piRNA-54265 theoretically, which was 29 nt (like a forward primer 1 in Table 3 below), the cDNA of the piRNA-54265 formed by reverse transcription could also be specifically amplified. On the other hand, when appropriately reducing the length of the forward primers, i.e., reducing the number of bases of the forward primers complementary with the cDNA, the forward primers could also be quantitatively amplified, but when the complementary bases were reduced to a certain number, the forward primers could not be effectively amplified. Therefore, under the premise of ensuring efficient amplification, we discussed the minimum number of the bases of the forward primers complementary with the cDNA. The numbers of the bases of the designed forward primers complementary with a terminal of a cDNA3' was sequentially decreased, which were 29, 25, 21, 17, 13, 9, 5, 4, 3, 2 and 1 respectively. The primer sequences were shown in Table 3 and Table 4 below. Corresponding amplification curves and melting curves were shown in FIGS. 12a~12b and FIGS. 13a~13b. It could be seen that the forward primer of the piRNA-54265 could be effectively amplified from the last base at the terminal of 3, from 3' to 5' when the bases continuously complementary with the terminal of the cDNA3' were no less than 5 bases (TGGAG), and could not be effectively amplified when the complementary bases were 4, 3, 2, and 1 (i.e., the primer pairs in Table 3 and Table 4, and the primer pairs without TGGAG in the forward primers could not be effectively amplified).

TABLE 1 piRNA-54265 reverse transcription primer

| Serial No. | Note | Sequence | Sequence length (nt) |
|---|---|---|---|
| SEQ ID NO. 1 | piRNA-54265 | TGGAGGTGATGAACTGTCTGAG CCTGACC | 29 |
| SEQ ID NO. 2 | piRNA-54265 stem-loop reverse | TGACCGTCTGTATGGTTGTTCAC GACTCCTTCACCCTATCCAACCA | 67 |

TABLE 1-continued piRNA-54265 reverse transcription primer

| Serial No. | Note | Sequence | Sequence length (nt) |
|---|---|---|---|
| | transcription primer | TACAGACGGTCAGGTCAGGCT | |
| SEQ ID NO. 3 | piRNA-54265 PolyA tailed reverse transcription primer | GCTGTCAACGATACGCTACGTA ACGGCATGACAGTGT(24)A | 61 |
| SEQ ID NO. 4 | | GCTGTCAACGATACGCTACGTA ACGGCATGACAGTGT(24)G | 61 |
| SEQ ID NO. 5 | | GCTGTCAACGATACGCTACGTA ACGGCATGACAGTGT(24)C | 61 |

TABLE 2

External reference cel-miR-39 reverse transcription primer

| Serial No. | Note | Sequence | Sequence length (nt) |
|---|---|---|---|
| SEQ ID NO. 6 | cel-miR-39 sequence | TCACCGGGTGTAAATCAGCTTG | 22 |
| SEQ ID NO. 7 | cel-miR-39 stem-loop reverse transcription primer | TGAACATCCTCTGGAGGCCAAC TGCGTGAGCTTGTTACTCATTTT CTCAGCCTCCAGAGGATGTTCAC AAGCTGAT | 76 |
| SEQ ID NO. 3 | cel-miR-39 PolyA tailed reverse transcription primer | GCTGTCAACGATACGCTACGTA ACGGCATGACAGTGT(24)A | 61 |
| SEQ ID NO. 4 | | GCTGTCAACGATACGCTACGTA ACGGCATGACAGTGT(24)G | 61 |
| SEQ ID NO. 5 | | GCTGTCAACGATACGCTACGTA ACGGCATGACAGTGT(24)C | 61 |

TABLE 3 piRNA-54265 stem-loop PCR primer

| Serial No. | Note | Sequence | Sequence length (nt) |
|---|---|---|---|
| SEQ ID NO. 8 | piRNA-54265 stem-loop forward primer 1 | TGGAGGTGATGAACTGT CTGAGCCTGACC | 29 |
| SEQ ID NO. 9 | piRNA-54265 stem-loop reverse primer 1 | TATGGTTGTTCACGACT CCTTCAC | 24 |
| SEQ ID NO. 10 | piRNA-54265 stem-loop forward primer 2 | TGGAGGTGATGAACTGT CTGAGCCT | 25 |
| SEQ ID NO. 9 | piRNA-54265 stem-loop reverse primer 2 | TATGGTTGTTCACGACT CCTTCAC | 24 |
| SEQ ID NO. 11 | piRNA-54265 stem-loop forward primer 3 | TGGAGGTGATGAACTGT CTGA | 21 |
| SEQ ID NO. 9 | piRNA-54265 stem-loop reverse primer 3 | TATGGTTGTTCACGACT CCTTCAC | 24 |
| SEQ ID NO. 12 | piRNA-54265 stem-loop forward primer 4 | TGGAGGTGATGAACTGT | 17 |
| SEQ ID NO. 13 | piRNA-54265 stem-loop reverse primer 4 | TATGGTTGTTCACGACT | 17 |
| SEQ ID NO. 14 | piRNA-54265 stem-loop forward primer 5 | TGGAGGTGATGAA | 13 |
| SEQ ID NO. 13 | piRNA-54265 stem-loop reverse primer 5 | TATGGTTGTTCACGACT | 17 |
| SEQ ID NO. 15 | piRNA-54265 stem-loop forward primer 6 | CTATCGCATGCTGGAGG TGA | 20 |

TABLE 3-continued piRNA-54265 stem-loop PCR primer

| Serial No. | Note | Sequence | Sequence length (nt) |
|---|---|---|---|
| SEQ ID NO. 13 | piRNA-54265 stem-loop reverse primer 6 | TATGGTTGTTCACGACT | 17 |
| SEQ ID NO. 16 | piRNA-54265 stem-loop forward primer 7 | TCGACTATCGCATGCTGGAG | 20 |
| SEQ ID NO. 13 | piRNA-54265 stem-loop reverse primer 7 | TATGGTTGTTCACGACT | 17 |
| SEQ ID NO. 17 | piRNA-54265 stem-loop forward primer 8 | TCGACTATCGCATGCTGGA | 19 |
| SEQ ID NO. 13 | piRNA-54265 stem-loop reverse primer 8 | TATGGTTGTTCACGACT | 17 |
| SEQ ID NO. 18 | piRNA-54265 stem-loop forward primer 9 | TCGACTATCGCATGCTGG | 18 |
| SEQ ID NO. 13 | piRNA-54265 stem-loop reverse primer 9 | TATGGTTGTTCACGACT | 17 |
| SEQ ID NO. 19 | piRNA-54265 stem-loop forward primer 10 | TCGACTATCGCATGCTG | 17 |
| SEQ ID NO. 13 | piRNA-54265 stem-loop reverse primer 10 | TATGGTTGTTCACGACT | 17 |
| SEQ ID NO. 20 | piRNA-54265 stem-loop forward primer 11 | TCGACTATCGCATGCT | 16 |
| SEQ ID NO. 13 | piRNA-54265 stem-loop reverse primer 11 | TATGGTTGTTCACGACT | 17 |

TABLE 4 piRNA-54265 PolyA tailed PCR primer

| Serial No. | Note | Sequence | Sequence length (nt) |
|---|---|---|---|
| SEQ ID NO. 8 | piRNA-54265 PolyA tailed forward primer 1 | TGGAGGTGATGAACTGTCTGAGCCTGACC | 29 |
| SEQ ID NO. 21 | piRNA-54265 PolyA tailed reverse primer 1 | GCTGTCAACGATACGCTACGTAACG | 25 |
| SEQ ID NO. 10 | piRNA-54265 PolyA tailed forward primer 2 | TGGAGGTGATGAACTGTCTGAGCCT | 25 |
| SEQ ID NO. 21 | piRNA-54265 PolyA tailed reverse primer 2 | GCTGTCAACGATACGCTACGTAACG | 25 |
| SEQ ID NO. 11 | piRNA-54265 PolyA tailed forward primer 3 | TGGAGGTGATGAACTGTCTGA | 21 |
| SEQ ID NO. 22 | piRNA-54265 PolyA tailed reverse primer 3 | GCTGTCAACGATACGCTACG | 20 |
| SEQ ID NO. 12 | piRNA-54265 PolyA tailed forward primer 4 | TGGAGGTGATGAACTGT | 17 |
| SEQ ID NO. 22 | piRNA-54265 PolyA tailed reverse primer 4 | GCTGTCAACGATACGCTACG | 20 |
| SEQ ID NO. 14 | piRNA-54265 PolyA tailed forward primer 5 | TGGAGGTGATGAA | 13 |
| SEQ ID NO. 23 | piRNA-54265 PolyA tailed reverse primer 5 | GCTGTCAACGATACG | 15 |
| SEQ ID NO. 15 | piRNA-54265 PolyA tailed forward primer 6 | CTATCGCATGCTGGAGGTGA | 20 |

TABLE 4-continued piRNA-54265 PolyA tailed PCR primer

| Serial No. | Note | Sequence | Sequence length (nt) |
|---|---|---|---|
| SEQ ID NO. 22 | piRNA-54265 PolyA tailed reverse primer 6 | GCTGTCAACGATACGCTACG | 20 |
| SEQ ID NO. 16 | piRNA-54265 PolyA tailed forward primer 7 | TCGACTATCGCATGCTGGAG | 20 |
| SEQ ID NO. 22 | piRNA-54265 PolyA tailed reverse primer 7 | GCTGTCAACGATACGCTACG | 20 |
| SEQ ID NO. 17 | piRNA-54265 PolyA tailed forward primer 8 | TCGACTATCGCATGCTGGA | 19 |
| SEQ ID NO. 22 | piRNA-54265 PolyA tailed reverse primer 8 | GCTGTCAACGATACGCTACG | 20 |
| SEQ ID NO. 18 | piRNA-54265 PolyA tailed forward primer 9 | TCGACTATCGCATGCTGG | 18 |
| SEQ ID NO. 22 | piRNA-54265 PolyA tailed reverse primer 9 | GCTGTCAACGATACGCTACG | 20 |
| SEQ ID NO. 19 | piRNA-54265 PolyA tailed forward primer 10 | TCGACTATCGCATGCTG | 17 |
| SEQ ID NO. 22 | piRNA-54265 PolyA tailed reverse primer 10 | GCTGTCAACGATACGCTACG | 20 |
| SEQ ID NO. 20 | piRNA-54265 PolyA tailed forward primer 11 | TCGACTATCGCATGCT | 16 |
| SEQ ID NO. 22 | piRNA-54265 PolyA tailed reverse primer 11 | GCTGTCAACGATACGCTACG | 20 |

TABLE 5

External reference cel-miR-39 stem-loop PCR primer

| Serial No. | Note | Sequence | Sequence length (nt) |
|---|---|---|---|
| SEQ ID NO. 24 | cel-miR-39stem-loop forward primer | CGGCTCACCGGGTGTAAATC | 20 |
| SEQ ID NO. 25 | cel-miR-39stem-loop reverse primer | CAACTGCGTGAGCTTGTTACTC | 22 |

TABLE 6

External reference cel-miR-39PolyA tailed PCR primer

| Serial No. | Note | Sequence | Sequence length (nt) |
|---|---|---|---|
| SEQ ID NO. 24 | cel-miR-39PolyA tailed forward primer | CGGCTCACCGGGTGTAAATC | 20 |
| SEQ ID NO. 22 | cel-miR-39PolyA tailed reverse primer | GCTGTCAACGATACGCTACG | 20 |

2. Further optimization of primers:

According to the results of FIGS. 12 and 13, the amplification efficiencies of the third stem-loop primer pair (i.e., corresponding to SEQ TD NO:11&9) and the fourth PolyA tailed primer pair (i.e., corresponding to SEQ TD NO:11&22) were higher than that of other primers, so these two pairs of primers were selected as candidate primers with higher preference.

Figure 14:
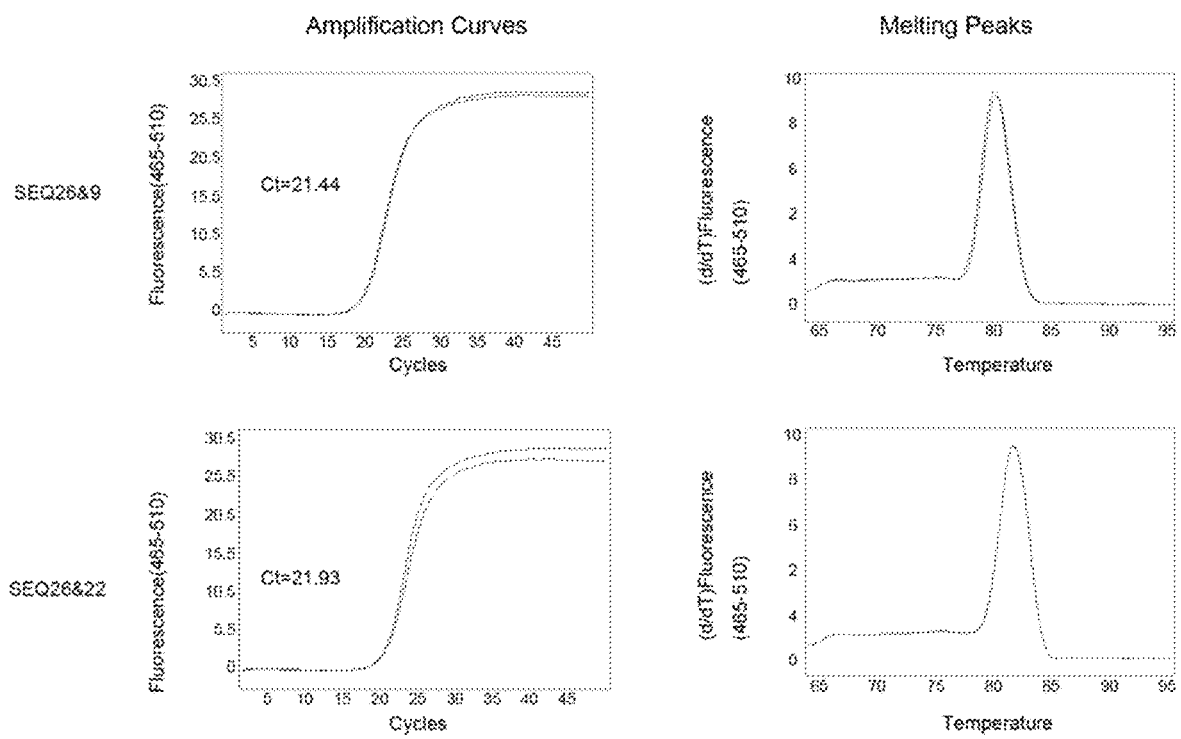
FIG. 14 shows amplification curves and melting curves of the optimal primers of the stem-loop method and the PolyA tailed method.

Based on the candidate optimal primers screened above, C and G were introduced at the 5' end of the primer for further optimization. The optimized primer sequences were shown in Tables 7 and 8 below, and the corresponding amplification curves and melting curves were shown in FIG. 14.

TABLE 7

Optimal stem-loop primer pair

| Serial No. | Note | Sequence | Sequence length (nt) |
| --- | --- | --- | --- |
| SEQ ID NO. 26 | piRNA-54265 stem-loop forward primer 12 | CCTGGAGGTGATGAACTGTCTG | 22 |
| SEQ ID NO. 9 | piRNA-54265 stem-loop reverse primer 12 | TATGGTTGTTCACGACTCCTTCAC | 24 |

TABLE 8

Optimal PolyA tailed primer pair

| Serial No. | Note | Sequence | Sequence length (nt) |
| --- | --- | --- | --- |
| SEQ ID NO. 26 | piRNA-54265 PolyA tailed forward primer 12 | CCTGGAGGTGATGAACTGTCTG | 22 |
| SEQ ID NO. 22 | piRNA-54265 PolyA tailed reverse primer 12 | GCTGTCAACGATACGCTACG | 20 |

3. Digital PCR platform detection involved the use of probes, corresponding probes were designed according to the optimal primer, as shown in Table 9:

TABLE 9

Stem-loop probe

| Serial No. | Note | Sequence | Sequence length (nt) |
| --- | --- | --- | --- |
| SEQ ID NO. 27 | piRNA-54265 stem-loop probe | FAM-CCCTATCCAACCATACAGACGGTCAGG-BHQ1 | 27 |
| SEQ ID NO. 28 | cel-miR-39 stem-loop probe | HEX-ATTTTCTCAGCCTCCAGAGGATGTTCA-BHQ1 | 27 |

Embodiment 12 piRNA-54265 Detection Method

1. Total RNA extraction from specimen:
(1) Total RNA extraction from serum:
1) 100 μl of plasma (serum) was added to a reaction plate.
2) A proteinase K digestion, wherein a digestion system was: 45 μl of proteinase K digestion buffer, 5 μl of proteinase K (50 mg/ml), and a total volume of 50 μl.
3) A mixture was shaken up and incubated for 5 minutes on a vortexer; incubated for 30 minutes at 65° C.; and then shaken up and incubated for 5 minutes on the vortexer at 700 rpm.
4) A lysis &RNA binding system (Lysis Binding Mix) was prepared: 99 μl of lysis buffer, 1 μl of 2-mercaptoethanol, and a total volume of 100 μl.
5) 100 μl of the Lysis Binding Mix, 5 fmol of external reference cel-miR-39, and 20 μl of magnetic beads (RNA Binding Beads) were sequentially added.
6) The mixture was shaken up and incubated for 7 minutes on the vortexer at 400 rpm.
7) The mixture was eluted by isopropanol, shaken up and incubated for 15 minutes on the vortexer.
8) The mixture was reversed and blended again like step 7).
9) The reaction plate was placed on a magnetic stand until the solution was clear; and a supernatant was discarded.
10) 180 μl of complete eluent 1 (complete eluent 1:10 ml of isopropanol was added into an eluent 1) was added and the reaction plate was shaken up on the vortexer for 1 minute at 700 rpm.
11) The reaction plate was placed on the magnetic stand for 1 minute until the solution became clear; and a supernatant was discarded.
12) Steps 10) and 11) were repeated with 180 μl of complete eluent 2 (complete eluent 2:48 ml of absolute ethyl alcohol was added in an eluent 2).
13) The mixture was placed on the vortexer and spin-dried for 5 minutes.
14) DNAzymes was added for digestion, wherein a digestion system was: 48 μl of DNase buffer, 2 μl of DNase (20 U/μl), and a total volume of 50 μl.

15) After being film-pasted, the mixture was placed on the vortexer and shaken up for 15 minutes.

16) 50 μl of rebinding buffer and 100 μl of isopropanol were respectively added successively. The mixture was shaken up for 5 minutes on the vortexer.

17) The reaction plate was placed on the magnetic stand for 5 minutes until the solution became clear; and a supernatant was discarded.

18) 180 μl of complete eluent 2 was added and film-pasted, and the reaction plate was shaken up on the vortexer for 30 seconds at 700 rpm.

19) The reaction plate was placed on the magnetic stand for 1 minute until the solution became clear; and a supernatant was discarded.

20) Steps 18) and 19) were repeated.

21) The mixture was air-dried on the vortexer for 5 minutes.

22) 50 μl of enzyme-free water (Elution Buffer) preheated to 65° C. was added, and then the reaction plate was shaken up on the vortexer for 2 minutes.

23) The reaction plate was placed in a water bath at 65° C. for incubation for 5 minutes.

24) The reaction plate was placed on the magnetic stand until the solution became clear; and a supernatant (extracted RNA) was transferred to an enzyme-free tube and stored at −80° C.

(2) Total RNA extraction from urine specimen:

1) 50 μl of urine specimen was added into a reaction plate.

2) A lysis &RNA binding system (Lysis Binding Mix) (one specimen hole) was prepared: 198 μl of lysis buffer, 2 μl of β-mercaptoethanol, and a total volume of 200 μl.

3) 200 μl of Lysis Binding Mix was added into the reaction plate in step 2), and a final volume was adjusted to 450 μl, then the reaction plate was sealed with a film, and shaken up and blended on a vortexer for 7 minutes at 300 rpm.

4) 30 μl of magnetic bead binding system was added into the reaction plate, wherein the magnetic bead binding system (one specimen hole) was: 20 μl of RNA binding magnetic beads, 10 μl of lysis/binding promoting solution, and a total volume of 30 μl.

5) The reaction plate was sealed with a film, shaken up and blended on the vortexer for 5 minutes at 300 rpm.

6) The mixture was eluted by isopropanol, then shaken up and blended for 20 minutes on the vortexer.

7) The reaction plate was placed on a magnetic stand until the solution was clear; and a supernatant was discarded.

8) 180 μl of complete eluent 1 was added, and the reaction plate was sealed with a film and blended on the vortexer for 1 minute at 700 rpm.

9) The reaction plate was placed on the magnetic stand until the solution became clear; and a supernatant was discarded.

10) Steps 8) and 9) were repeated with a complete eluent 2.

11) The mixture was spin-dried on the vortexer for 5 minutes.

12) DNAzymes was added for digestion, and a digestion system was: 48 μl of DNase buffer, 2 μl of DNase (20 U/μl), and a total volume of 50 μl, sealed with a film, and then shaken up for incubation for 15 minutes;

13) 50 μl of rebinding buffer and 100 μl of isopropanol were sequentially added into the reaction plate.

14) The reaction plate was sealed with a film, and shaken up for 5 minutes on the vortexer.

15) The reaction plate was placed on the magnetic stand until the reaction solution became clear, and a supernatant was discarded.

16) 180 μl of complete eluent 2 was added, and the reaction plate was shaken up on the vortexer for 30 seconds.

17) The reaction plate was placed on the magnetic stand until the reaction solution became clear; and a supernatant was discarded.

18) Steps 16) and 17) were repeated with the complete eluent 2.

19) The reaction plate was spin-dried on the vortexer for 5 minutes.

20) 50 μl of enzyme-free water preheated to 65° C. was added, then the reaction plate was sealed with a film and placed on the vortexer for incubation for 2 minutes.

21) The reaction plate was put into a water bath for incubation at 65° C. for 5 minutes.

22) The reaction plate was placed on the vortexer for incubation for 2 minutes.

23) The reaction plate was placed on the magnetic stand until the solution became clear; and a supernatant was transferred to an enzyme-free tube and stored at −80° C.

2. Reverse Transcription:

(1) First-Strand Synthesis of cDNA by Stem-Loop Reverse Transcription:

1) A reverse transcription system was prepared as shown in Table 10 below (for each specimen):

TABLE 10

Stem-loop reverse transcription system

| Constituent | Volume (μl) |
|---|---|
| 5 × reverse transcription reaction buffer[1] (5 × Reaction Buffer) | 4 |
| 10 mM deoxyribonucleotide mixture[2] (10 mM dNTPMix) | 2 |
| Moloney murine leukemia virus reverse transcriptase with low H activity of RNase (200 U/μl RevertAid ™ M-MuLV Reverse Transcriptase) | 1 |
| RNase inhibitor (20 U/μl RNase Inhibitor) | 1 |
| piRNA-54265 reverse transcription primer (10 pmol/μl) | 1 |
| cel-miR-39 reverse transcription primer (10 pmol/μl) | 1 |
| Reverse transcription system | 10 |

Remarks: [1] The 5×reverse transcription reaction buffer was formulated by tris(hydroxymethyl) aminomethane, i.e., Tris-HCl (pH=8.3), potassium chloride (KCl), magnesium chloride ($MgCl_2$), and dithiothreitol (DTT). [2] 10 mM deoxyribonucleotide mixture contained four deoxyribonucleotides dATP, dCTP, dGTP and dTTP at a concentration of 10 mM, and was dissolved in 0.6 mM Tris-HCl buffer (pH=7.5).

2) 10 μl of RNA was extracted from the 50 μl of total RNA extracted, and then added into 10 μl of the reverse transcription system above, and detached. The mixture was placed in a temperature cycler for reverse transcription: 60 minutes at 42° C., and 5 minutes at 70° C.

3) The first-strand of the cDNA synthesized by reverse transcription could be placed on ice for standby service or stored at −20° C. for a long time.

(2) First-Strand Synthesis of cDNA by PolyA Tailed Reverse Transcription:

1) A PolyA tail was added to RNA, and a tail was added to the RNA in the specimen according to a reaction system in Table 11 below, and incubated at 37° C. for 10 minutes.

TABLE 11

| Constituent | Volume (μl) |
|---|---|
| Polyadenine nucleotide polymerase (5000 U/ml) | 1 |
| 10 × polyadenine nucleotide polymerization reaction buffer | 2 |
| RNase inhibitor | 1 |
| 10 mM ATP | 2 |
| RNA | 1-10 μg |
| RNase-free water | made up to a volume of 20 μl |
| Total volume | 20 |

2) First-Strand Synthesis of cDNA by Reverse Transcription:

Reverse transcription was performed on the RNA already added with the PolyA tail in 1), and a reverse transcription reaction system was configured as shown in Table 12 below.

TABLE 12

| Constituent | Volume (μl) |
|---|---|
| RNA added with PolyA tail | 10 |
| 5 × reverse transcription reaction buffer (5 × Reaction Buffer) | 4 |
| 10 mM deoxyribonucleotide mixture (10 mM dNTP Mix) | 2 |
| Moloney murine leukemia virus reverse transcriptase with low H activity of RNase (200 U/μl RevertAid ™ M-MuLV Reverse Transcriptase) | 1 |
| RNase inhibitor (20 U/μl RNase Inhibitor) | 1 |
| Reverse transcription primer mixture (10 pmol/μl) | 1 |
| Enzyme-free water | 1 |
| Total volume | 20 |

3. PCR Detection:

(1) Real-Time Fluorescence Quantitative PCR:

1) Reaction System:

cDNA stock solution was appropriately diluted and subjected to quantitative PCR. The target piRNA, external references and reaction system were shown in Tables 13 and 14 below, with 2 to 3 repetition respectively:

TABLE 13

| Constituent | Volume (μl) | Final concentration |
|---|---|---|
| 2 × SYBR GREEN | 5 | 1× |
| piRNA-54265 forward primer (10 pmol/μl) | 1 | 1 pmol/μl |
| piRNA-52465 reverse primer (10 pmol/μl) | 1 | 1 pmol/μl |
| Water | 2 | — |
| cDNA of appropriate dilution ratio | 1 | — |
| Quantitative PCR system | 10 | — |

TABLE 14

| Constituent | Volume (μl) | Final concentration |
|---|---|---|
| 2 × SYBR GREEN | 5 | 1× |
| cel-miR-39 forward primer (10 pmol/μl) | 1 | 1 pmol/μl |
| cel-miR-39 reverse primer (10 pmol/μl) | 1 | 1 pmol/μl |
| Water | 2 | — |
| cDNA of appropriate dilution ratio | 1 | — |
| Quantitative PCR system | 10 | — |

2) PCR Amplification Reaction:

9 μl buffer of the reaction system was added into each hole of the PCR reaction plate, and then 1 μl cDNA of appropriate dilution ratio was added to perform the amplification reaction according to Table 15 below.

TABLE 15

| Step | | Temperature | Time | Cycle |
|---|---|---|---|---|
| Pre-denaturizing | | 95° C. | 5 minutes | 1 |
| Amplifying | Denaturizing | 95° C. | 10 seconds | 45 |
| | Annealing | 60° C. | 10 seconds | |
| | Extending | 72° C. | 10 seconds | |
| Melting curve | | 95° C. | 5 seconds | 1 |
| | | 65° C. | 1 minute | |
| | | 97° C. | — | |
| Cooling | | 40° C. | 30 seconds | 1 |

3) Analysis of Results:

The PCR amplification results were represented by CT values, which were defined as the number of cycles in the PCR reaction system when fluorescence signals reached a set threshold. A relative expression level of a target gene of the specimen was calculated by $\Delta CT_{target} = CT_{target} - CT_{control}$, where $CT_{target}$ was the CT value of piRNA-54265, and $CT_{control}$ was the CT value of the former cel-miR-39 of the same specimen, so the relative expression of the target gene = $2^{-\Delta CT_{target}}$.

(2) Digital PCR (Based on a Bia-Rad Platform for Example):

1) A nucleic acid content of the specimen added in 20 ul of cDNA system with an appropriate concentration should not exceed the detection range specified by digital PCR (1 to 100,000 copies of fragmented nucleic acid or 1 to 20,000 copies of complete genome DNA), and was generally 50 fg to 100 ng.

2) Configurations of the digital PCR reaction system were shown in Table 16 below.

TABLE 16

| Constituent | Volume (μl) |
|---|---|
| ddPCRProbe Supermix (no dUTP) | 10 |
| piRNA-54265 forward primer | 1 |
| piRNA-54265 reverse primer | 1 |
| cel-miR-39 forward primer | 1 |
| cel-miR-39 reverse primer | 1 |
| piRNA-54265 probe | 1 |
| cel-miR-39probe | 1 |
| cDNA with appropriate concentration | 1 |
| Water | 3 |
| Total | 20 |

3) After the above system configurations was completed, a digital PCR droplet generator was enabled, a film-sealing machine was preheated, and a water-in-oil droplet generating cartridge were prepared; then 20 μl of the above-mentioned system in Table 16 and 70 μl of droplet-forming oil were respectively added to avoid the generation of bubbles.

4) After a droplet-generating sealing pad was added, the mixture was put into the digital PCR droplet generator to start generating droplets.

5) After the water-in-oil droplets were completely generated, 40 μl of the water-in-oil droplets were removed to a PCR reaction plate.

6) After the droplets were completely removed, the droplets were sealed with an aluminum film. After the film was sealed, an amplification reaction was carried out according to Table 17:

TABLE 17

| Step | Temperature | Time | Cycle |
|---|---|---|---|
| Enzyme activating | 95° C. | 5 minutes | 1 |
| Denaturizing | 94° C. | 30 seconds | 40 |
| Extending | 60° C. | 1 minute | |
| Enzyme deactivating | 98° C. | 10 minutes | 1 |
| Cooling | 12° C. | Remained | — |

7) The whole PCR process took about 1 hour and 45 minutes. A droplet reader was enabled to rinse and set the parameters. After the amplification was completed, the PCR reaction plate was placed on the droplet reader to read the results.

Embodiment 13 Kit Assembly

1. A piRNA-54265 detection kit used for early screening, diagnosis, efficacy monitoring and/or prognostic evaluation of colorectal cancer including a piRNA-54265 detection primer pair.

The primer pair includes a forward primer and a reverse primer. The forward primer is designed based on the sequence of the piRNA-54265 (which changes U in the RNA sequence of the piRNA-54265 to T), and sequentially includes an amount of bases from the 5'- of the sequence, and shall include the first five bases "TGGAG" at least. The primer pair is a piRNA-54265 stem-loop PCR primer pair, or a piRNA-54265 PolyA tailed PCR primer pair.

Preferably, the piRNA-54265 stem-loop PCR primer pair is shown as SEQ ID NO:8/9, SEQ ID NO:10/9, SEQ ID NO:11/9, SEQ ID NO:12/13, SEQ ID NO:14/13, SEQ ID NO:15/13, SEQ ID NO:16/13, SEQ ID NO:17/13, SEQ ID NO:18/13, SEQ ID NO:19/13 or SEQ ID NO:20/13.

Preferably, the piRNA-54265 PolyA tailed PCR primer pair is shown as SEQ ID NO:8/21, SEQ ID NO:10/21, SEQ ID NO:11/22, SEQ ID NO:12/22, SEQ ID NO:14/23, SEQ ID NO:15/22, SEQ ID NO:16/22, SEQ ID NO:17/22, SEQ ID NO:18/22, SEQ ID NO:19/22 or SEQ ID NO:20/22.

Most preferably, the forward primer and the reverse primer of the piRNA-54265 stem-loop PCR primer pair are respectively shown as SEQ ID NO:26 and SEQ ID NO:9.

Most preferably, the forward primer and the reverse primer of the piRNA-54265 PolyA tailed PCR primer pair are respectively shown as SEQ ID NO:26 and SEQ ID NO:22.

The probe sequence is show as SEQ ID NO:27.

A piRNA-54265 stem-loop reverse transcription primer sequence is shown as SEQ ID NO:2.

A piRNA-54265 PolyA tailed reverse transcription primer sequence is shown as SEQ ID NO:3:5.

2. The method of using the kit is as described in the embodiment 12.

Embodiment 14 Specimen Detection Via Kit

1. Source of Specimen:

After obtaining the informed consent of the patients, serum specimens of colorectal cancer patients diagnosed pathologically from 2016 to 2018 in the Sun Yat-Sen University Cancer Center and serum specimens without malignant tumors found in the Cancer Prevention Physical Examination Center were collected.

2. Serum piRNA-54265 levels of normal people, colorectal cancer patients before onset, people with high-grade intraepithelial neoplasia in colorectum, and colorectal cancer patients were detected.

(1) According to the method in the Embodiment 12, RNAs of the serum specimens were extracted, and then subjected to stem-loop reverse transcription, and fluorescence quantitative PCR detection.

Figures 15A, 15B:
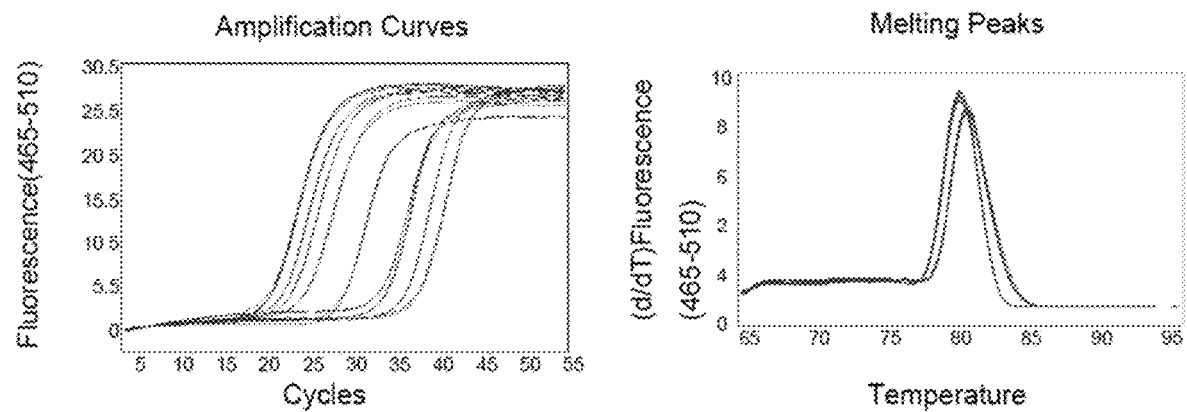
FIGS. 15a~15b show serum piRNA-54265 levels of one healthy control (normal people) during the follow-up visit via real-time fluorescence quantitative PCR detection of a kit, and one CRC case during the follow-up visit (not found cancer at the time of sampling, before the onset of colorectal cancer), one sample with high-grade intraepithelial neoplasia in colorectum and two cases of colorectal cancer patients (stage I and IV).

(2) The results were shown in FIGS. 15a~15b. FIG. 15a showed amplification curves of serum piRNA-54265 and external reference cel-miR-39 of one non-tumor control (CONTROL) during the follow-up visit, one CRCcase (CASE) (no cancer at the time of sampling), one case of high-grade intraepithelial neoplasia in colorectum, and two cases of colorectal cancer patients (stage I and IV).

$\Delta CT_{CRC1\ Average}=6.09$, $\Delta Ct_{CRC2\ Average}=10.19$, $\Delta Ct_{HIN\ Average}=13.84$, $\Delta Ct_{CASE\ Average}=15.17$, and $\Delta Ct_{CONTROL\ Average}=19.88$.

The larger the $\Delta Ct$, the lower the relative expression amount was. It could be seen that the serum piRNA-54265 level of the colorectal cancer patients was significantly higher than that of the normal people and the high-grade intraepithelial neoplasia patient. In addition, the serum piRNA-54265 level of patients with colorectal cancer before diagnosis was also higher than that of the control that no colorectal cancer was detected in later period.

3. The serum piRNA-54265 levels of the colorectal cancer patients before operation, and in the first day, third day, fifth day, and seventh day after the operation were detected.

(1) According to the method in the Embodiment 12, RNAs of the serum specimens were extracted, and then subjected to stem-loop reverse transcription, and fluorescence quantitative PCR detection.

Figure 16A:
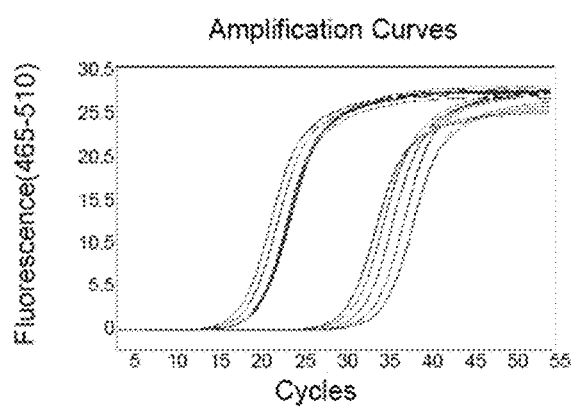
FIGS. 16a~16b show the serum piRNA-54265 levels of colorectal cancer patients before operation, and in the first day, the third day, the fifth day and the seventh day after operation via the real-time fluorescence quantitative PCR detection of the kit.
Figure 16B:
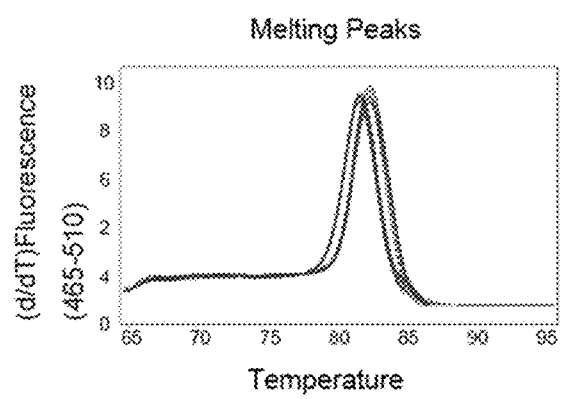

(2) The results were shown in FIG. 16, which showed the serum piRNA-54265 levels of the colorectal cancer patients before operation, and in the first day, the third day, the fifth day and the seventh day after operation. FIG. 16a showed amplification curves of the serum piRNA-54265 and external reference cel-miR-39 of the patients before operation, and in the first day, the third day, the fifth day and the seventh day after operation as well as external reference cel-miR-39. $\Delta Ct_{before\ operation}=6.57$, $\Delta Ct_{in\ the\ first\ day\ after\ operation}=7.31$, $\Delta Ct_{in\ the\ third\ day\ after\ operation}=8.49$, $\Delta Ct_{in\ the\ fifth\ day\ after\ operation}=10.67$, $\Delta Ct_{in\ the\ seventh\ day\ after\ operation}=12.12$. The smaller the $\Delta Ct$, the larger the relative expression amount was. It could be seen that the serum piRNA-54265 levels decreased after operation, and the piRNA-54265 levels also gradually decreased with the increase of days after operation.

4. Quantitative detection was performed on the serum piRNA-54265 levels based on a Bio-rad digital PCR platform.

(1) According to the method in the Embodiment 12, RNAs of the serum specimens were extracted, and then subjected to stem-loop reverse transcription, and digital PCR detection.

Figure 17:
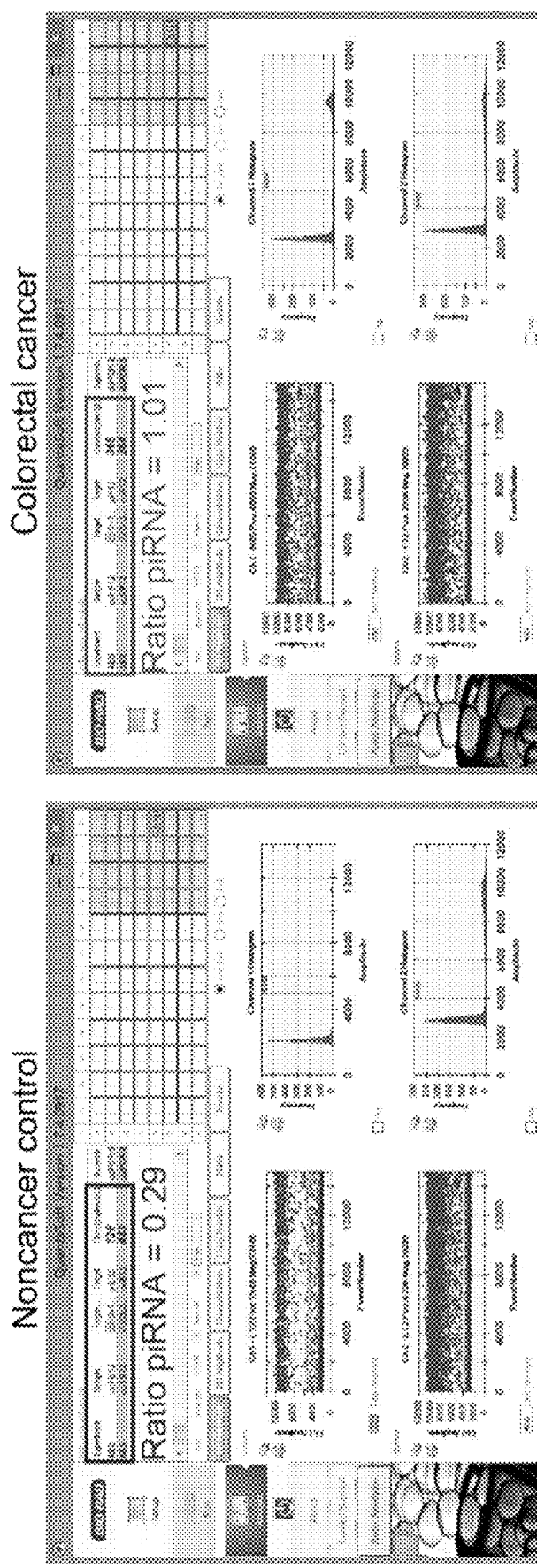
FIG. 17 shows the serum piRNA-54265 levels in normal people and colorectal cancer patients before treatment via digital PCR detection of the kit.

(2) The results were as shown in FIG. 17, wherein the expression of the piRNA-54265 could be detected both in the serums of the normal people and the colorectal cancer patients. After correction by reference genes, the expression levels of the piRNA-54265 in the serums of the colorectal cancer patients were significantly higher than that of the control set.

Embodiment 15 Efficacy Evaluation of piRNA-54265 Detection Kit

The experiment was designed to detect a specific amount of exogenous synthesized piRNA-54265 analog added into a negative serum, perform RNA extraction, reverse transcription and quantitative PCR detection by the kit, investigate whether detection values of the kit accord with the real values (a specific amount exogenously added) as well as amplification efficiency and specificity of each primer designed under a primer design model provided by the kit.

Specific experimental method: an exogenously synthesized piRNA-54265 mimic (mimic analog) was completely identical in sequence and structure to piRNA-54265 in a natural serum. A specific total amount of piRNA-54265 mimic (5 fmol) was added into 100 μl of negative serum (fetal calf serum), and then subjected to subsequent extraction and detection according to the kit (external reference was required). The results were calculated according to the recovery calibration on the Ct values and the external reference.

Figure 18A:
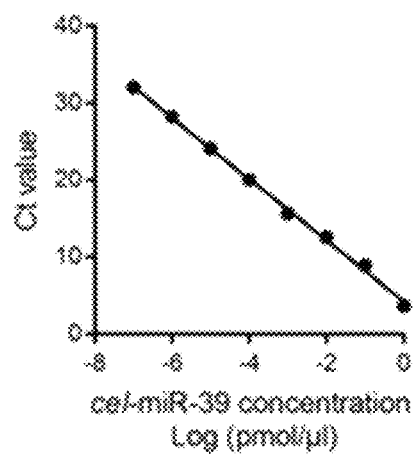
FIGS. 18a~18d show the efficacy evaluation of the piRNA-54265 detection kit.
Figure 18B:
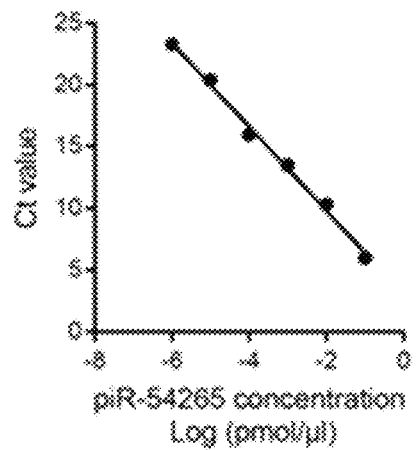
Figure 18C:
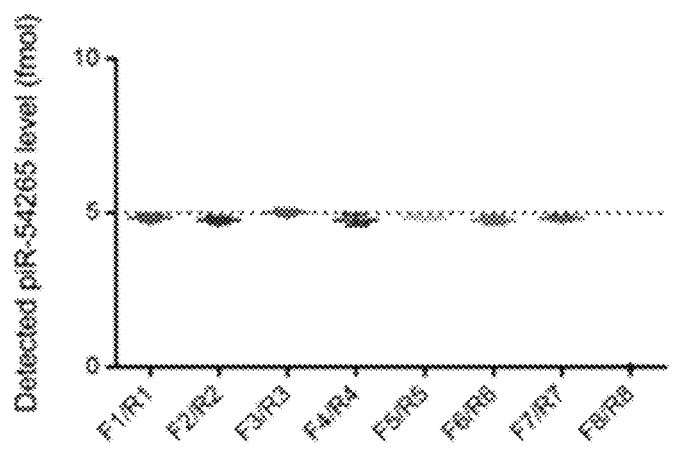
Figure 18D:
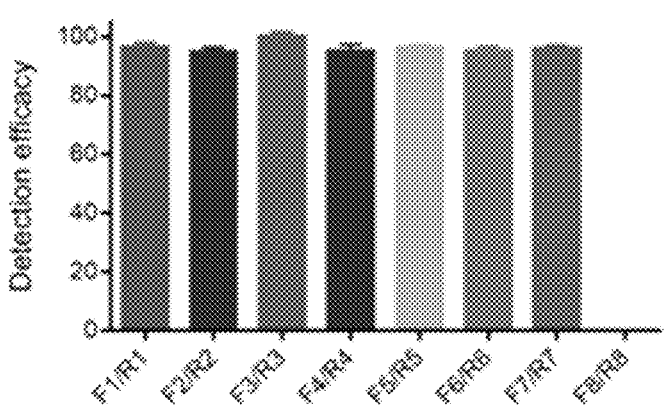

The results were shown in FIGS. 18a~18d. FIG. 18a and FIG. 18b showed standard curves of cel-miR-39 and piRNA-54265 standards with different concentrations. FIG. 18c showed the piRNA-54265 level corrected after calculating the recovery. The recovery was calculated by reference to the Ct value of the cel-miR-39 detected by kit extraction of fetal bovine serum specimens added with a certain amount of cel-miR-39 and the Ct value obtained by reverse transcription PCR to the cel-miR-39 standards of the same amount without extraction. FIG. 18d was to evaluate the detection efficiencies of different primer pairs in FIG. 18c.

Upon the detections conducted by the kit, as shown in FIG. 18b, each detection result was close to the true value level, and all the detection efficiencies were above 90%, as shown in FIG. 18d. Meanwhile, the primer pairs designed on the basis of the primer design model provided by the kit had both excellent amplification efficiency and specificity (F1/R1 to F7/R7).

What is claimed is:

1. A composition comprising a primer pair and probe for specifically detecting piRNA-54265, wherein said primer pair is selected from:
   (a) a first primer pair for amplifying piRNA-54265 containing a stem loop comprising a forward primer consisting of the nucleotide sequence of SEQ ID NO: 26 and a reverse primer consisting of the nucleotide sequence of SEQ ID NO: 9 and
   (b) a second primer pair for amplifying a poly-A tailed piRNA-54265 comprising a forward primer consisting of the nucleotide sequence of SEQ ID NO: 26 and a reverse primer consisting of the nucleotide sequence of SEQ ID NO: 22; and
   wherein said probe consists of the nucleotide sequence of SEQ ID NO: 27.

2. The composition according to claim 1, further comprising a primer for reverse transcription.

3. The composition according to claim 2, wherein the primer for reverse transcription is for reverse transcribing a piRNA-54265 containing a stem loop and wherein the primer for reverse transcription consists of the nucleotide sequence of SEQ ID NO: 2.

4. A piRNA-54265 detection kit, comprising the composition according to claim 3.

5. The composition according to claim 2, wherein the primer for reverse transcription is for reverse transcribing a poly-A tailed piRNA-54265 and wherein the primer for reverse transcription consists of one of the nucleotide sequences selected from SEQ ID NOs: 3-5.

6. A piRNA-54265 detection kit, comprising the composition according to claim 5.

7. A piRNA-54265 detection kit, comprising the composition according to claim 2.

8. A piRNA-54265 detection kit, comprising the composition according to claim 1.

* * * * *